United States Patent
Mayo et al.

(10) Patent No.: US 11,033,709 B2
(45) Date of Patent: Jun. 15, 2021

(54) SYSTEM AND METHOD FOR REDUCING STRESS

(71) Applicant: VMAS Solutions Inc., Scottsdale, AZ (US)

(72) Inventors: Vicki Mayo, Scottsdale, AZ (US); Amy Serin, Scottsdale, AZ (US); Jack Maxwell Vice, Orlando, FL (US)

(73) Assignee: VMAS Solutions Inc., Scottsdale, AZ (US)

( * ) Notice: Subject to any disclaimer, the term of this patent is extended or adjusted under 35 U.S.C. 154(b) by 87 days.

(21) Appl. No.: 16/191,242

(22) Filed: Nov. 14, 2018

(65) Prior Publication Data

US 2020/0147339 A1 May 14, 2020

(51) Int. Cl.
*A61M 21/02* (2006.01)
*A61M 21/00* (2006.01)

(52) U.S. Cl.
CPC ..... *A61M 21/02* (2013.01); *A61M 2021/0022* (2013.01); *A61M 2205/0294* (2013.01); *A61M 2205/3327* (2013.01); *A61M 2205/3584* (2013.01); *A61M 2205/50* (2013.01); *A61M 2205/8206* (2013.01); *A61M 2230/06* (2013.01); *A61M 2230/50* (2013.01)

(58) Field of Classification Search
CPC .............................................. A61M 21/00–02
See application file for complete search history.

(56) References Cited

U.S. PATENT DOCUMENTS

| | | | |
|---|---|---|---|
| 6,001,073 A | 12/1999 | Schmidt et al. | |
| 6,409,655 B1 | 6/2002 | Wilson et al. | |
| 10,512,750 B1 * | 12/2019 | Lewin Jessen | A61M 21/02 |
| 2002/0035995 A1 | 3/2002 | Schmidt et al. | |
| 2011/0190594 A1 * | 8/2011 | Heit | A61B 5/4815 |
| | | | 600/301 |
| 2011/0290252 A1 * | 12/2011 | Amjad | A61M 16/026 |
| | | | 128/204.23 |

(Continued)

OTHER PUBLICATIONS

European Patent Office International Searching Authority, International Search Report and Writte Opinion in International Application No. PCT/US2017/027046 dated Jul. 12, 2017.

(Continued)

*Primary Examiner* — Thaddeus B Cox
(74) *Attorney, Agent, or Firm* — Transformative Legal, LLC; Len S. Smith; Julie E. Kurzrok

(57) ABSTRACT

A method for providing a therapeutic benefit to a person is disclosed which includes a processor that executes a first function to determine a physiological parameter from one or more physiological sensors positioned on the person and then the processor executes a second function to determine at least one second physiological parameter from the one or more physiological sensors or an environmental parameter from one or more environmental sensors associated with the location of the person. Next, the processor uses either the first and second physiological parameters or the first physiological parameter and the environmental parameter to determine whether to apply bi-lateral stimulation to the person; activating first and second stimulators positioned bi-laterally on the person to initiate bi-lateral stimulation for a therapeutically effective time period when the processor determines to apply bi-lateral stimulation.

18 Claims, 26 Drawing Sheets

(56) References Cited

U.S. PATENT DOCUMENTS

| | | | |
|---|---|---|---|
| 2012/0157895 A1 | 6/2012 | Barlow et al. | |
| 2012/0197337 A1 | 8/2012 | Su et al. | |
| 2014/0179986 A1 | 6/2014 | Kelley | |
| 2017/0124276 A1* | 5/2017 | Tee | G08B 21/0453 |
| 2017/0296429 A1* | 10/2017 | Mayo | A61H 23/02 |
| 2017/0368329 A1* | 12/2017 | Tyler | A61N 1/36036 |
| 2018/0318545 A1* | 11/2018 | Jones | A61M 21/02 |
| 2020/0281525 A1* | 9/2020 | Mills | A61B 5/0533 |

OTHER PUBLICATIONS

International Search Report based on PCT/US2018/063008 filed Nov. 29, 2018, dated Dec. 7, 2019.
Athar, Faroog, "How to Use Moving Average Filter to Counter Noisy Data Signal?", Dec. 4, 2017, Retrieved from Internet: https://medium.com/blueeast/how-to-use-moving-average-filter-to-counter-noisy-data-signal-5b530294a12e [retrieved on Feb. 18, 2021].
Anonymous: "Kalman filter—Wikipedia", Nov. 1, 2018, Retrieved from Internet: https//en.wikipedia.org/w/index.php?title_Kalman_filter$oldid=866849029 [archived Apr. 4, 2019 Web page retrieved on Feb. 18, 2021].

\* cited by examiner

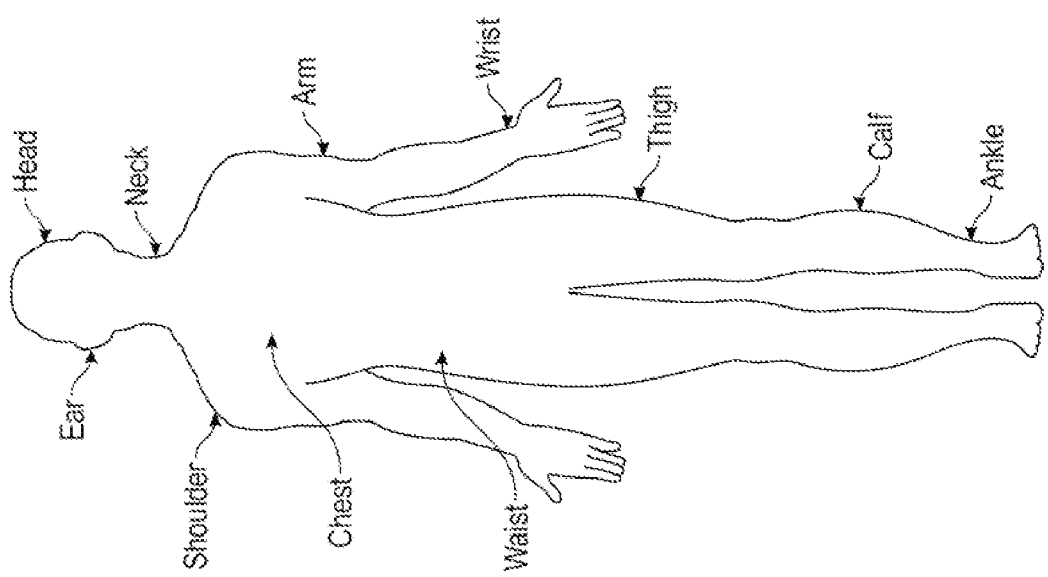

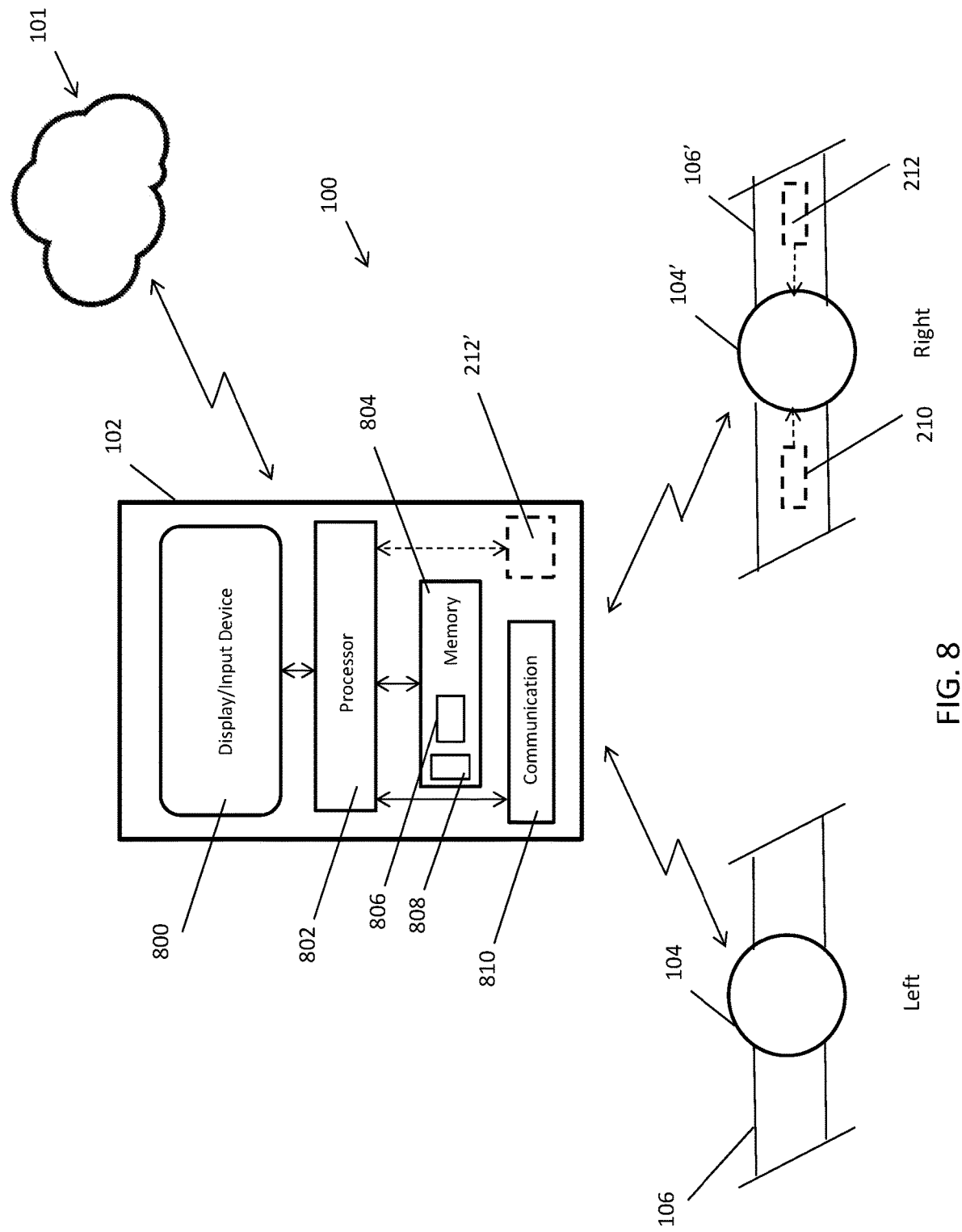

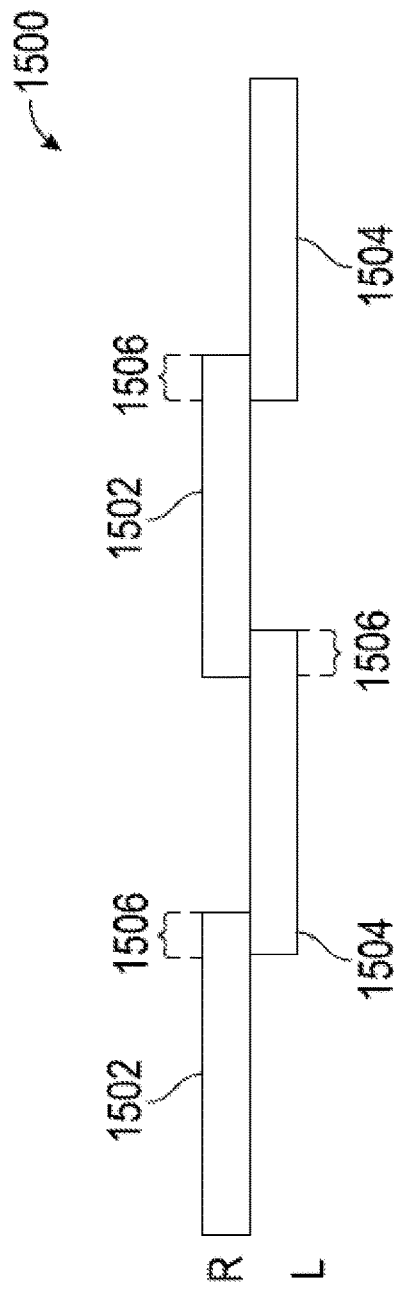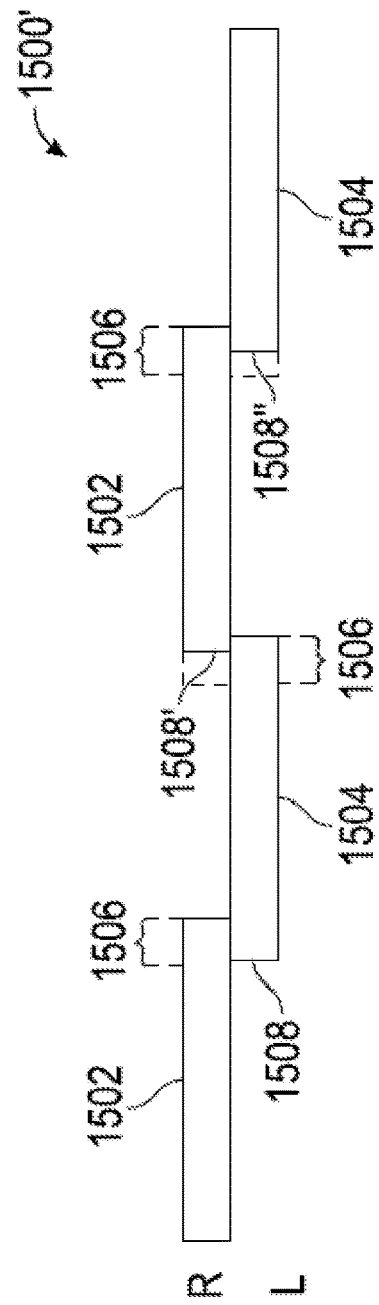
FIG. 15A
FIG. 15B

SYSTEM AND METHOD FOR REDUCING STRESS

TECHNICAL FIELD

The technical field generally relates to stress reduction, and more particularly relates to a system and method for reducing stress to improve performance.

BACKGROUND

Stress is one of the most pervasive psychological complaints. Stress has been linked to digestive distress, headaches, depression, sleep problems, weight gain, underachievement, panic, avoidance, and poor physical health. When sensory information or thoughts are integrated in the brain and trigger the sympathetic nervous system, performance worsens. Returning an individual to a calm state as soon as possible is desirable. Once acute stress is experienced over time, the brain develops neural "habits" that overemphasize the stress response. Stress is known to increase body inflammation and is considered to be the root cause of significant suffering, often impeding performance and the ability to carry out normal daily activities to one's potential.

In many adults, chronic stress begins in childhood from genetic predispositions, and/or traumatic physical or emotional distress. Stress adversely impacts brain development and creates over activation of the sympathetic nervous system, resulting in performance degradation, preoccupation, depression, anxiety, over-reactivity, and sub-optimal functioning in other areas of the brain. The brain's structure and function can be significantly altered in ways that promote ongoing stress and less adaptability. The more stress experienced in childhood has been shown to correlate with a number of negative outcomes related not only to psychological problems, but also physical disease and mortality.

Accordingly, it is desirable to provide methods and systems for disrupting the brain's habit of over-activating the sympathetic nervous system. It is further desirable that the systems and methods are easy to use and do not impede individual's mobility or performance of their job or other everyday tasks. It is still further desirable that the systems and methods can be used intermittently (manually) as desired or automatically upon detection or anticipation of a stressful state of a person. Other desirable features and characteristics will become apparent from the subsequent summary and detailed description and the appended claims, taken in conjunction with the accompanying drawings and the foregoing technical field and background.

BRIEF SUMMARY

Various non-limiting embodiments of an alternating bi-lateral stimulation system and method for providing a therapeutic benefit to a person are disclosed herein.

In a first non-limiting embodiment, a method for providing a therapeutic benefit to a person, includes, but is not limited to, a processor executing a first function to determine a physiological parameter from one or more physiological sensors positioned on the person and then the processor executing a second function to determine at least one or a second physiological parameter from the one or more physiological sensors or an environmental parameter from one or more environmental sensors associated with a location of the person. Next, the processor uses either the first and second physiological parameters or the first physiological parameter and the environmental parameter to determine whether to apply bi-lateral stimulation to the person; activating first and second stimulators positioned bi-laterally on the person to initiate bi-lateral stimulation for a therapeutically effective time period when the processor determines to apply bi-lateral stimulation.

In another non-limiting embodiment, a system for providing a therapeutic benefit to a person includes, but is not limited to, first and second tactile stimulators bi-laterally positioned in therapeutic contact with a body of a person, a plurality of physiological sensors coupled to the first and second tactile stimulators and a plurality of environmental sensors coupled to the first and second tactile stimulators. A processor communicably coupled to the first and second tactile simulators, the plurality of physiological and the plurality of environmental sensors, is configured to (i) execute a first function to determine a physiological parameter from one or more physiological sensors positioned on the person; (ii) execute a second function to determine at least one of a second physiological parameter from the one or more physiological sensors or an environmental parameter from one or more environmental sensors associated with a location of the person; (iii) determine, using either the first and second physiological parameters or the first physiologic parameter and the environmental parameter, whether to apply bi-lateral stimulation to the person; and (iv) activate the first and second stimulators positioned bi-laterally on the person to initiate bi-lateral stimulation for a therapeutically effective time period when the processor determines to apply bi-lateral stimulation.

DESCRIPTION OF THE DRAWINGS

Embodiments of the present invention will hereinafter be described in conjunction with the following drawing figures, where like numerals denote like elements, and:

FIG. 5C illustrates various locations on a person for placement of stimulation elements in accordance with a non-limiting embodiment;

FIG. 8 is another illustration of the bi-lateral stimulation system in operation in accordance with a non-limiting embodiment;

FIGS. 15A-15C are illustrations of timing diagrams for applying stimulation via the stimulation elements in accordance with non-limiting embodiments;

DETAILED DESCRIPTION

As used herein, the word "exemplary" means "serving as an example, instance, or illustration." The following detailed description is merely exemplary in nature and is not intended to limit application and uses. Any embodiment described herein as "exemplary" is not necessarily to be construed as preferred or advantageous over other embodiments. All of the embodiments described in this Detailed Description are exemplary embodiments provided to enable persons skilled in the art to make or use the embodiment and not to limit the scope that is defined by the claims. Furthermore, there is no intention to be bound by any expressed or implied theory presented in the preceding Technical Field, Background, Drawings Summary or the following Detailed Description.

Figure 1:
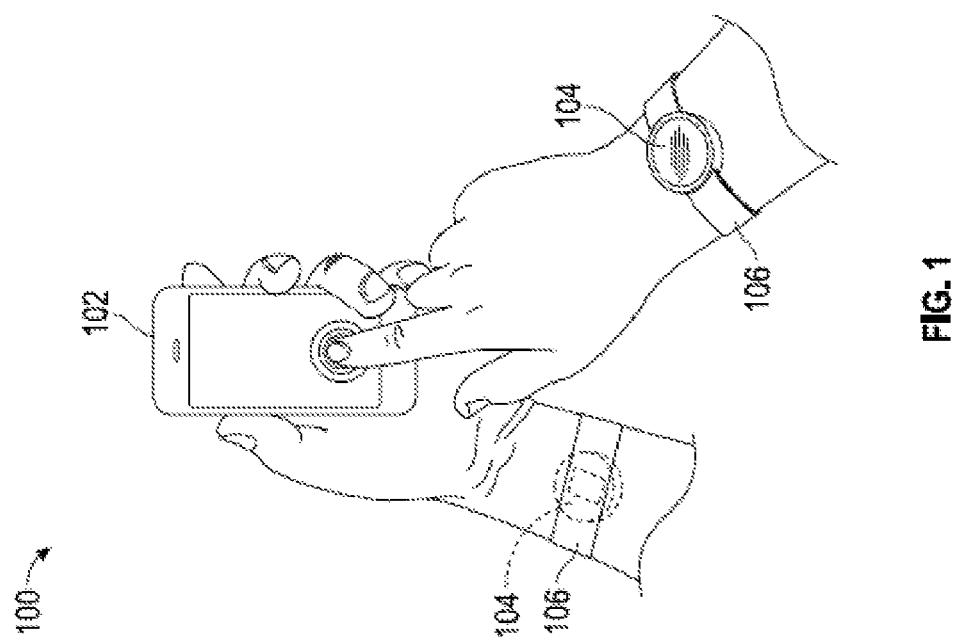
FIG. 1 is an illustration of a bi-lateral stimulation system in accordance with a non-limiting embodiment.

FIG. 1 is an illustration of a bi-lateral stimulation system 100 in accordance with a non-limiting embodiment. The stimulation system 100 is said to be bi-lateral, as stimulation is applied to opposing sides of individual's body. In the embodiment illustrated in FIG. 1, vibrating elements 104 are coupled to the individual's wrists by a band 106. The vibrating elements 104 are controlled by a mobile device 102 (e.g., cell phone, tablet computer, personal digital assistant or remote-control device) running a software application (or app) that wirelessly communicates with the vibrating elements 104 via the mobile device 102 causing them to vibrate. In a manual mode of operation, an individual may activate bi-lateral stimulation by operating the mobile device 102, including manually programming various stimulation parameters for the bi-lateral stimulation. The mobile device 102, in turn, operates the vibrating elements 104 to provide the bi-lateral stimulation to the person wearing the vibrating elements 104. In an automatic mode of operation, a processor in the mobile device 102 executes functions or algorithms running to determine and monitor one or more physiological and environmental parameters to determine whether an individual is experiencing (or about to experience) an increase in stress, and then automatically activate bi-lateral stimulation. In some embodiments, the automatic bi-lateral stimulation is applied responsive to the one or more physiological parameters and/or environmental parameters exceeding a threshold indicative that the individual is experiencing (or about to experience) an increase in stress. The automatic bi-lateral stimulation is typically applied for a therapeutically effective predetermined period of time after which the one or more physiological parameters and/or environmental parameters are re-evaluated to determine if there is an indication that the stress (or potential stress) situation has been mitigated. As used here, "mitigate", "mitigated" or "mitigation" means that the parameters indicating that stress experienced (or is about to be experienced) by an individual has been sufficiently reduced to indicate some recovery from physiological stress. In this way, the automatic mode of operation is said to be "closed-loop" meaning that bi-lateral stimulation can be applied automatically (unless stopped by the person) via the monitoring and evaluation of physiological and environmental parameters by the processor.

In one exemplary embodiment, bi-lateral asynchronous stimulation is provided by the vibrating elements 104. As used herein, "asynchronous" means to stimulate each vibrating element 104 in an alternating manner with some period of overlap where both stimulating elements are vibrating simultaneously. The overlap area may begin randomly or may be programmed as will be discussed below. The vibrating elements 104 alter the brain's internal communication in multiple areas including the somatosensory cortex and other brain networks. This interferes with the brain's ability to activate the sympathetic nervous system and therefore reduces the stress response. By applying the bi-lateral and asynchronous stimulation to the individual's body, the individual experiences a reduction in stress and a lessening of distressing body sensations (e.g., racing heartbeat, stomach aches). Because the brain can activate sympathetic arousal in milliseconds, the overlap period provides an advantage over conventional bi-lateral stimulators because a stimulation gap commonly used in conventional bi-lateral stimulators could allow for the brain to activate the sympathetic system. The stimulation provided during the overlap period also enhances bi-lateral impact in the somatosensory areas of the individual's brain.

In another exemplary embodiment, continuous bi-lateral stimulation is provided by the vibrating elements 104. As used herein, "continuous" means to stimulate each vibrating element 104 in an alternating manner without any gap or pause between the stimulation being applied to opposing (bi-lateral) sides of the body. Similar to asynchronous stimulation, continuous bi-lateral stimulation alters the brain's internal communication in multiple areas including the somatosensory cortex and other brain networks continuously so as not to provide time for the brain to activate the sympathetic system.

Figure 2:
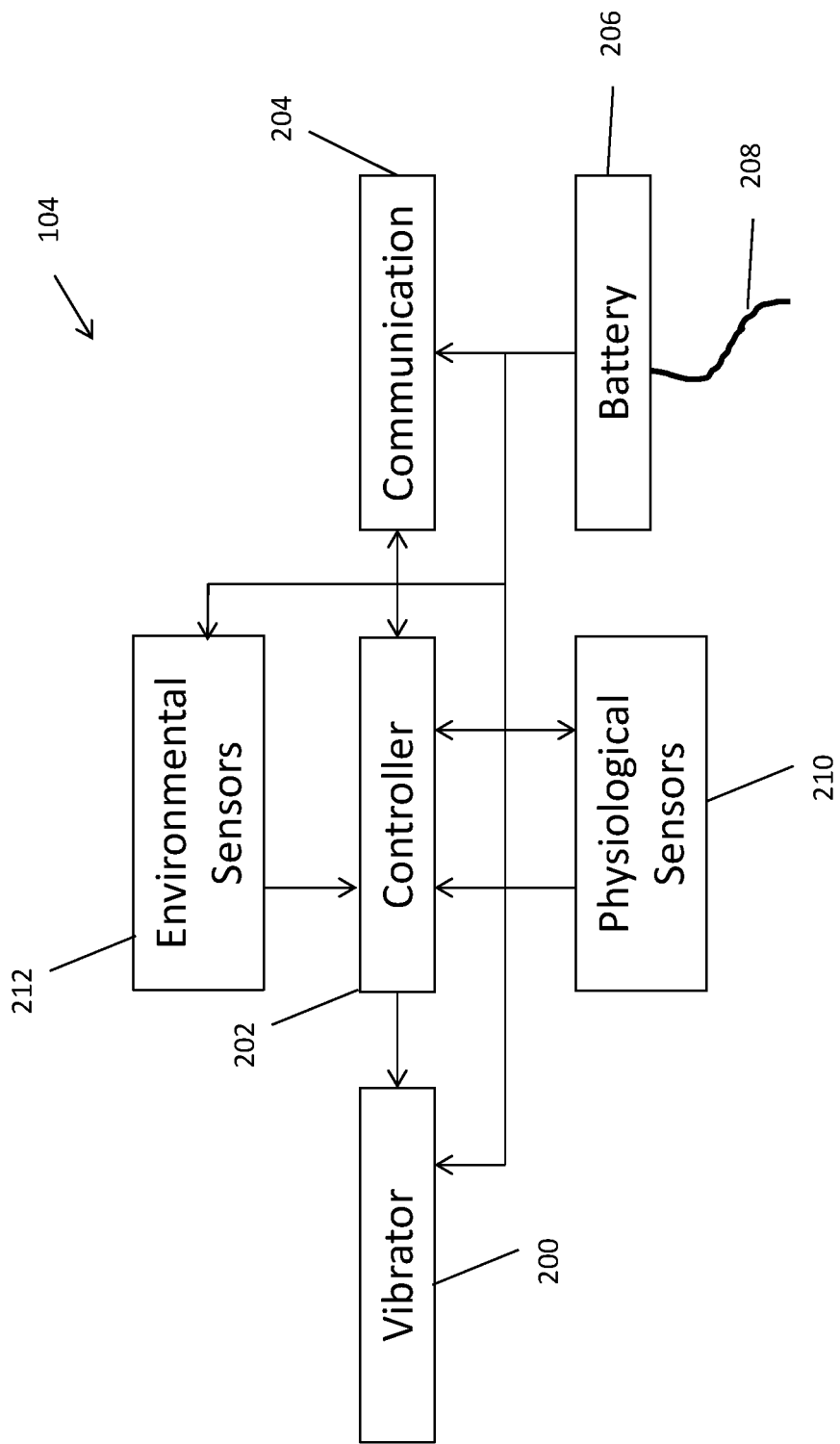
FIG. 2 is a block diagram of the stimulation elements of FIG. 1 in accordance with a non-limiting embodiment.

Referring now to FIG. 2, a block diagram of a vibrating element 104 is shown. The vibrating element 104 includes a vibrator 200, which in some embodiments is a piezoelectric vibrator as is known in the art. The vibrator 200 is controlled by a controller 202 which receives instructions via the communication module 204 from the mobile device 102 (see FIG. 1). A battery 206 provides power to each of the components of vibrating element 104. The battery 206 may utilize any suitable battery chemistry, including, but not limited to, alkali, metal-hydride, lithium and maybe rechargeable or replaceable depending upon the implementation in any given embodiment. In some embodiments, the battery 206 may be coupled via cable 208 to power or recharge the battery 206 from a supplemental power source (not shown in FIG. 2) such as the mobile device 102 (see, FIG. 1). The cable 208 may be fitted with a micro USB connector or other suitable connector as will be appreciated by those skilled in the art. The communication module 204 may be any form of low-power wireless communication (e.g., BLUETOOTH, WIFI). In some embodiments, controller 202 comprises one or more processors. The processor (s) may reside in single integrated circuit, such as a single or multi-core microprocessor, or any number of integrated circuit devices and/or circuit boards working in cooperation to accomplish the functions of the controller 202. The processor(s) may be a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. The controller 202 may also contain a memory system, such as non-volatile memory (e.g., Read Only Memory (ROM), flash memory, etc.), volatile memory (e.g., Dynamic Random Access Memory (DRAM)), or some combination of the two.

In accordance with exemplary embodiments, the controller 202 is also coupled to one or more physiological sensors 210 and environmental sensors 212. The physiological sensors 210 measure one or more (or a plurality) of physiological parameters of the individual employing the vibrating elements 104 to receive bi-lateral stimulation as will be discussed further in connection with FIG. 3. The environmental sensors 212 measure one or more (or a plurality) of environmental parameters surrounding and potentially impacting the individual using the vibrating elements 104 for bi-lateral stimulation as will be discussed further in connection with FIG. 4. The parameters measured by the physiological sensors 210 and the environmental sensors 212 are transmitted to the mobile device 102 via the communication module 204. In some embodiments, one of the vibrating elements 104 (for example, the right-side vibrating element) operates as the "master" sensor and the other vibrating element (the left-side vibrating element in this example) operates as a "slave" sensor. In some embodiments, the slave sensor can be used to verify, correlate or replace the master sensor in the event of a sensor failure. The mobile device 102 processes and analyzes the parameters using one or more algorithms or executable functions to determine physiological and environmental parameters and may determine to apply bi-lateral stimulation by comparing the parameters to one or more thresholds stored in memory in the mobile device 102. By determining physiological parameters and the environmental parameters from the master and/or slave sensors, the mobile device 102 is capable of automatically initiating bi-lateral stimulation to reduce or alleviate stress (or the potential onslaught of stress) in the individual.

Figure 3:
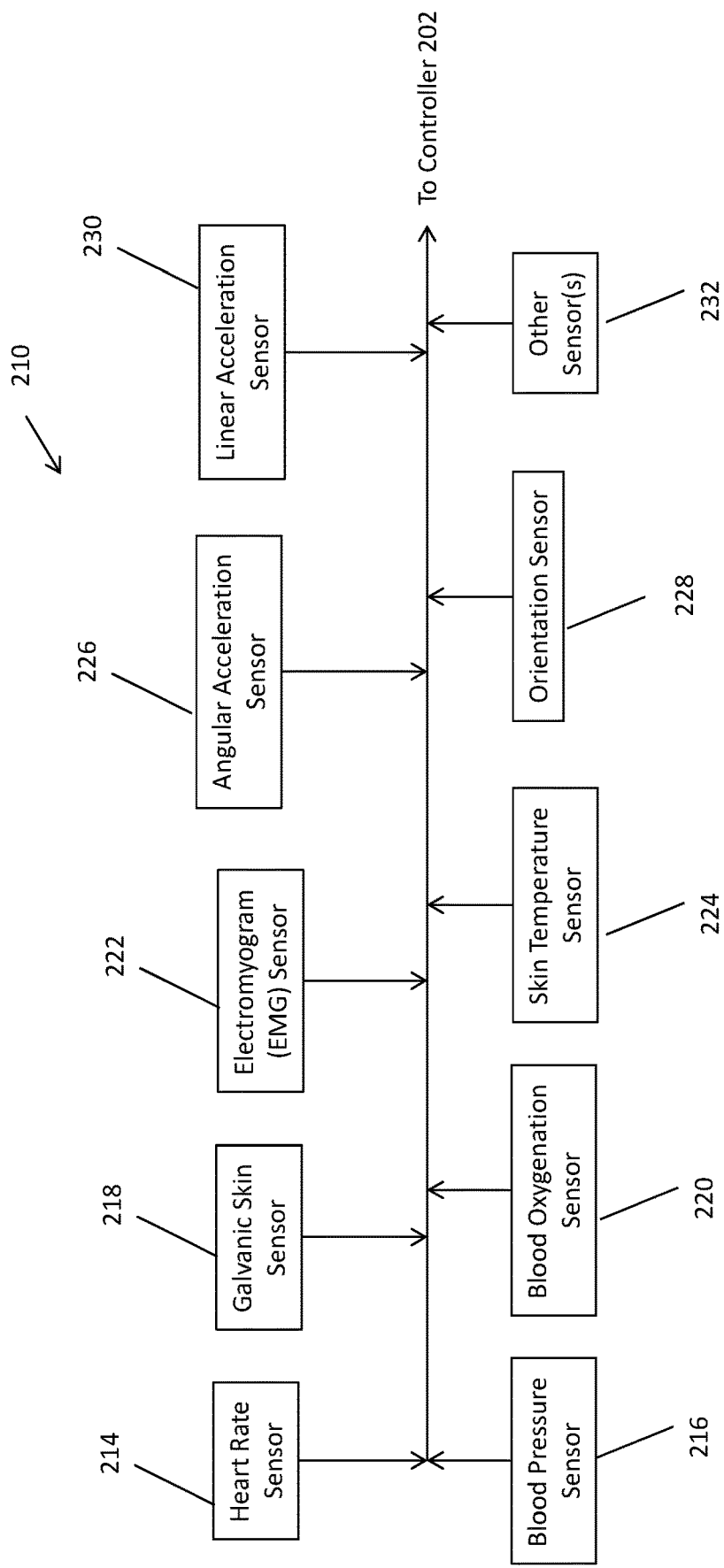
FIG. 3 is a block diagram of the physiological sensors of FIG. 2 in accordance with a non-limiting embodiment.

With continued reference to FIGS. 1-2. FIG. 3 is a block diagram of non-limiting examples of the physiological sensors 210. The physiological sensors 210 may include a heart rate sensor 214, a blood pressure sensor 216, a galvanic skin response sensor 218, a blood oxygenation sensor 220, an electromyogram (EMG) sensor 222, a skin temperature sensor 224, an angular acceleration sensor 226 for the vibrating element 104, and orientation sensor 228 for the vibrating element 104, a linear acceleration sensor 230 for the vibrating element 104, and any other sensors 232 as desired for any particular implementation of the physiological sensors 210. The use of the parameters measured by the physiological sensors 210 by the bi-lateral stimulation system 100 will be discussed further in connection with FIGS. 8-9 and FIGS. 18A-C.

Figure 4:
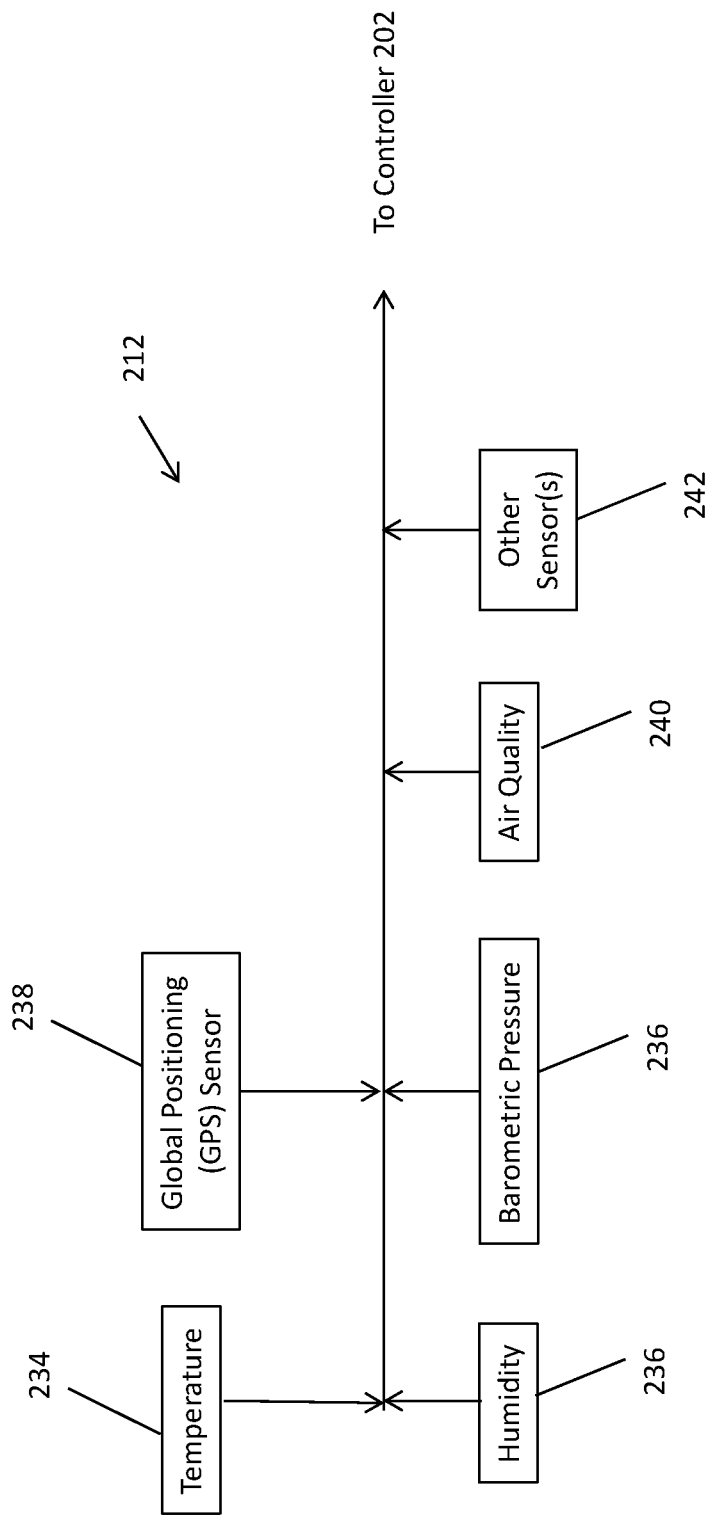
FIG. 4 is a block diagram of the environmental sensors of FIG. 2 in accordance with a non-limiting embodiment.

With continued reference to FIGS. 1-2. FIG. 4 is a block diagram of non-limiting examples of the environmental sensors 212. The environmental sensors 212 may include a temperature sensor 234, a humidity sensor 236, a global positioning sensor (GPS) 238, a barometric pressure sensor 239, an air quality sensor 240 and any other sensors 242 as may be desired any particular implementation. The use of the parameters measured by the environmental sensors 212 by the bi-lateral stimulation system 100 will be discussed further in connection with FIGS. 8-9 and FIGS. 18A-C.

Figure 5B:
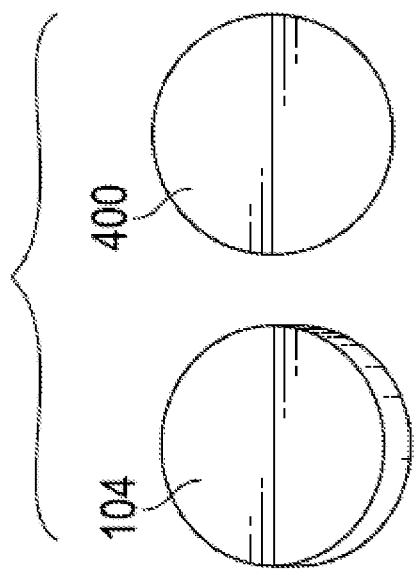
FIGS. 5A-5B are illustrations of non-limiting embodiments of the stimulation elements of FIG. 2.
Figure 5A:
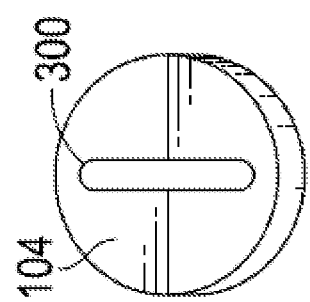

FIGS. 5A and 5B are illustrations of two non-limiting embodiments of the vibrating element 104. In FIG. 5A, the vibrating element 104 is a fixed with a clip 300 that an individual can attach to a band around a portion of individual's body (e.g., wrist, arm, chest, leg) to position the vibrating element 104 on an individual. In the embodiment illustrated in FIG. 5B, the vibrating element 104 may be temporarily positioned and fixed to an individual's body by a removable adhesive disc 400. Non-limiting examples of positions on a person for the vibrating elements may be temporarily positioned and fixed to an individual's body are illustrated in FIG. 5C. As used herein, a vibrating element 104 being brought into position or placed on individual body means being brought into "therapeutic contact" with an individual's body. Therapeutic contact may be achieved by direct contact (e.g., hand held, secured via adhesive or placed via a strap) or via indirect contact (e.g., through clothing, a coupling gel or through a wearable device). Accordingly, therapeutic contact means only that the individual need be able to perceive the stimulation provided by the bi-lateral vibrating elements 104 during therapy.

Figure 6B:
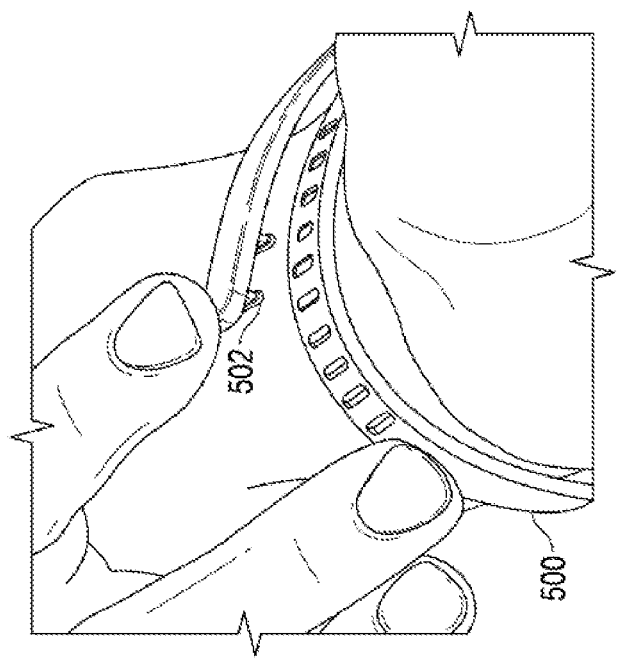
FIGS. 6A-6B are illustrations of securing bands that can be used with the stimulation elements of FIGS. 5A-5B in accordance with a non-limiting embodiment.
Figure 6A:
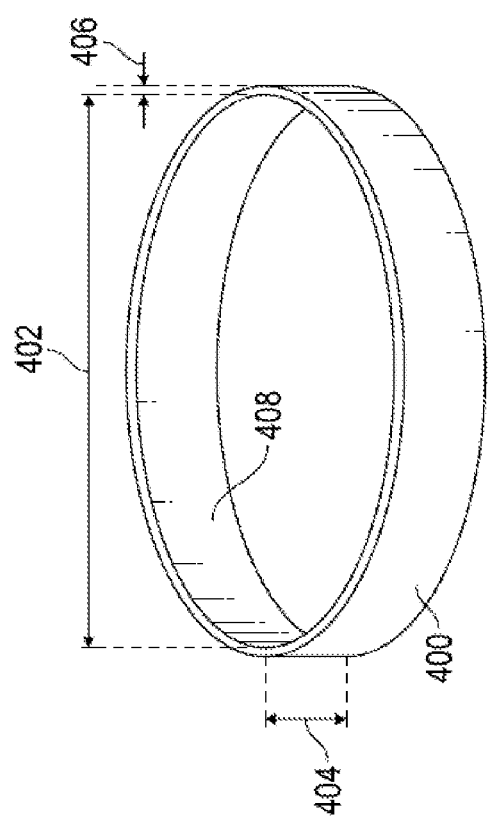

With continued reference to FIGS. 1-5, FIGS. 6A-B illustrate other non-limiting techniques for positioning a vibrating element 104 on an area of an individual's body. In FIG. 6A, a securing band 400 is shown. The securing band 400 may be compliant, elastic or may be secured using a hook-and-eye arrangement as is known in the art. The securing band 400 has a diameter 402, a height 404 and a thickness 406 sized suitably for the area of the individual's body (e.g., forehead, wrist, arm, chest, leg, ankle) that the band 400 will be placed around. The thickness 406 is also selected to facilitate attachment of the vibrating element 104 by the clip 300 (see FIG. 5A). The securing band 400 has an interior surface 408 upon which a material can be placed for the individual's comfort or to absorb moisture. In FIG. 6B, a wristband 500 is illustrated that may be used to position the vibrating elements 104 about an individual's wrist. The wristband 500 has an attachment mechanism 502 for securing the vibrating element 104 to the individual's wrist. The attachment mechanism 502 may be any suitable attachment mechanism such as those used to attach a wristwatch or fitness monitor to a person's wrist. In still other embodiments a hook-and-eye attachment mechanism maybe used as is known in the art.

Figure 7B:
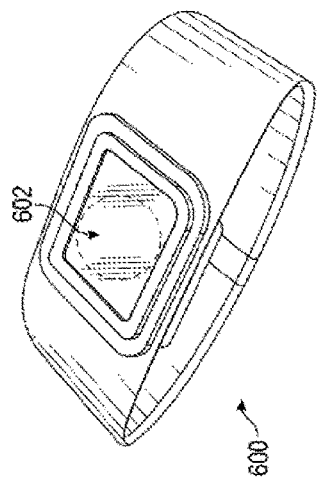
FIG. 7B is an illustration of a fitness monitor for use with the stimulation elements of FIG. 2 in accordance with a non-limiting embodiment.
Figure 7C:
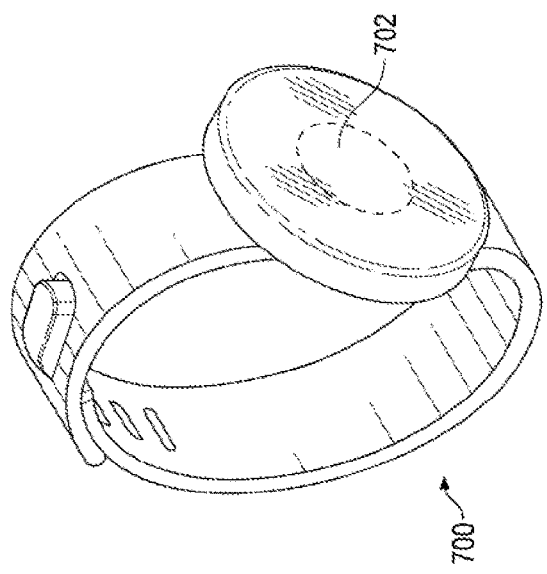
FIG. 7C is an illustration of a wristwatch for use with the stimulation elements of FIG. 2 in accordance with a non-limiting embodiment.
Figure 7A:
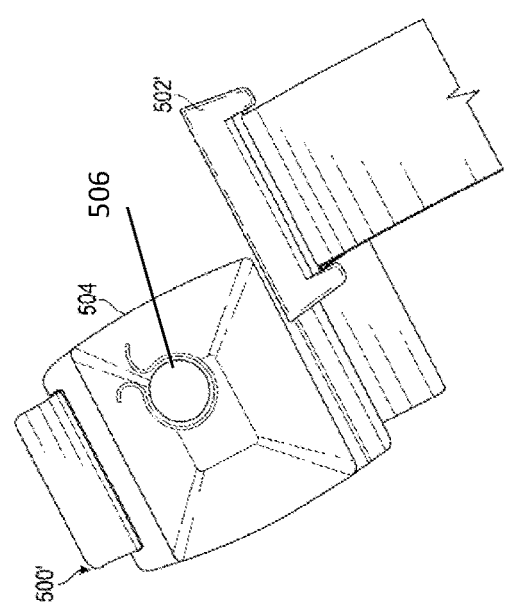
FIG. 7A are illustrations of a wristband that can be used with the stimulation element of FIG. 2 in accordance with a non-limiting embodiment.

With continued reference to FIGS. 1-5, FIGS. 7A-C other techniques for positioning a vibrating element 104 on a person. In FIG. 7A, a wristband 500' is illustrated for positioning a housing 504 containing a vibrating element 506 about an individual's wrist. The wristband 500' has a sliding attachment mechanism 502' for securing the housing 504 (and thus the vibrating element 506) to the individual's wrist. The wristband 500 or 500' may be formed of plastic, leather, fabric, metal or other suitable material and may be designed to be worn casually or as a fashion accessory. As will be appreciated, the vibrating elements 104 may also be combined into other devices. For example, FIG. 7B illustrates a wrist-worn fitness monitor 600 that includes a recess 602 on the interior portion of the device sized suitably to receive a vibrating element 104. The vibrating element 104 may be placed in the recess 602 by a friction-fit arrangement or by use of a removable adhesive disc (see FIG. 5B). Similarly, FIG. 7C illustrates a wristwatch 700 having a recess 702 on an interior portion to receive the vibrating element 104 as described above.

With continued reference to FIGS. 1-7, FIG. 8 illustrates a more detailed block diagram of the bi-lateral stimulation system 100 in accordance with the present disclosure. As discussed above in connection with FIG. 1, the mobile device 102 is in communication with a pair (left and right) of vibrating elements 104 to provide bi-lateral stimulation either in a manual mode or an automatic mode. In the manual mode, bi-lateral stimulation may be initiated selectively (on-demand) by an individual as will be discussed below in connection with FIGS. 10-17. In an automatic (closed-loop) mode, the mobile device 102 receives and processes the data from a plurality of environmental and physiological sensors received from one or both vibrating elements 104 (master sensor and/or master and slave sensor (s)) to process the sensor data using one or more functions or algorithms to determine whether a stressful situation exists (or is about to begin) and automatically initiate bi-lateral stimulation as will be discussed further in connection with FIG. 9 and FIGS. 18A-F.

The mobile device 102 may comprise any conventional mobile device (e.g., cell phone, tablet or personal digital assistant) capable of loading and running application programs (commonly referred to as "apps"). Generally, mobile device 102 will include an input output device 800 which may comprise a touch-sensitive display. User commands input and information output provided from into the display/input device 800 are processed by a processor 802. The processor 802 is in communication with a memory 804 which may include one or more application programs 806 one of which comprises a bi-lateral stimulation app configured to perform the methods discussed below in connection with FIG. 17 and FIGS. 18A-C. The memory 804 may also include a memory table 808 configured to align various physiological or environmental parameters with respective thresholds for use by the mobile device 102 in the automatic mode of bi-lateral stimulation. The mobile device 102 includes a communication module 810 that may communicate with the left and right vibrating elements (via communication module 204, see FIG. 2) as well as the cloud 101. As used herein, the "cloud" means a remote electronic data storage and processing facility that is accessed via the Internet and is commonly referred to metaphorically by those skilled in the art as residing in a cloud above the mobile device 102.

In some embodiments, the mobile device 102 indicates with the cloud 101 to transmit measured physiological environmental parameters associated with providing bilateral stimulation to the person. This information can be consolidated over time and used to provide updated information on when bilateral stimulation should be applied or modified to help alleviate stress in the person. Additionally, machine learning techniques can be applied to provide an updated parameter or stimulation model that the mobile device 102 can use in future bilateral stimulation sessions.

FIG. 8 also illustrates two non-limiting embodiments of the vibration elements. The left vibrating element 104 is shown coupled to a strap or band 106 that may be positioned on a wrist of an individual as discussed above. However, it will be appreciated that that these or additional vibrating elements 104 may be positioned in various places in the person as illustrated above in connection with FIG. 5C. In the illustrated embodiment, the vibrating element 104 contains all of the circuitry and elements discussed above in connection with FIG. 2. However, it will be appreciated that if additional slave sensing units are utilized in any particular embodiment, the additional slave sensors may comprise the circuitry elements discussed above in connection with FIG. 2 without the vibrator 200 to provide additional remote sensing. The right vibrating element 104' is illustrated coupled to a band or strap 106' where the physiological sensors 210 and the environmental sensors 212 have been separated from the remaining circuitry of the vibrating element 104' and incorporated into the band or strap 106'. Additionally, in some embodiments some or all of the environmental sensors 212 may be incorporated into the mobile device 102 as illustrated in optional element 212'.

Figure 9:
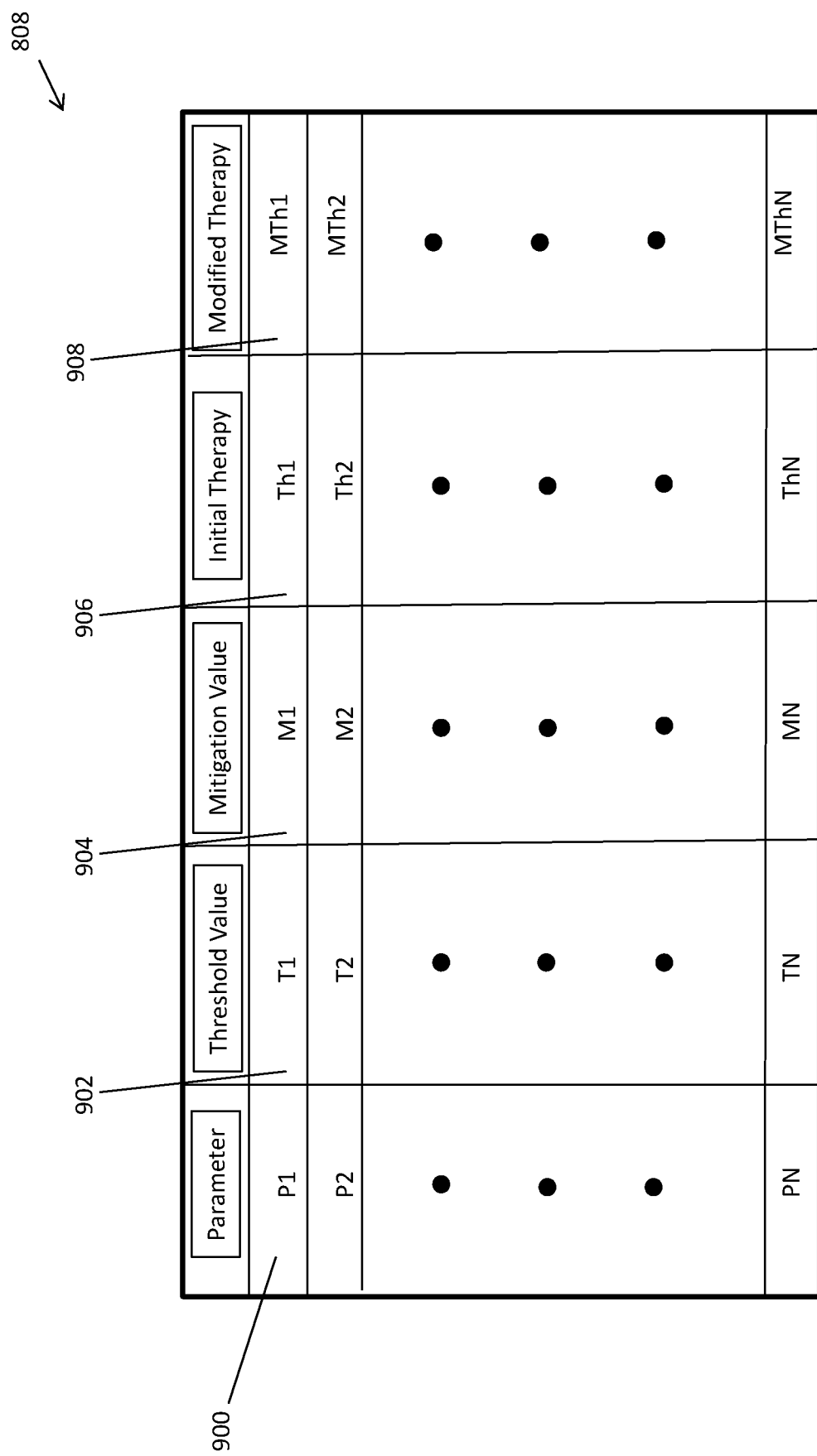
FIG. 9 is an illustration of a memory table for sensor and operational parameters for the bi-lateral stimulation system of FIG. 8 in accordance with non-limiting embodiments.

With continued reference to FIG. 8, FIG. 9 illustrates one non-limiting example of a memory table 808 configured to align physiological and environmental parameters with thresholds and respective responsive bi-lateral stimulation therapies that may be provided to an individual in an automatic mode. Initially, the entries of memory table 808 may be populated in with default values or more customize values entered by a therapist or caregiver treating the person for stress. Thereafter, some embodiments update one or more of the entries in memory table 808 based upon machine learning of the stress incidents detected in the person's response to one or more sessions of bi-lateral stimulation. In one embodiment, memory table 808 is organized to align measured parameter P1 (e.g., heart rate) 900 with threshold value T1 (for example, 100 bpm) 902 indicate to the mobile device 102 that bi-lateral stimulation should be commenced when P1 exceeds T1 and cease when P1 is equal to (or less than) a mitigation value M1 (e.g., 90 bpm) 904. The mitigation value M1 is selected (may be programmed) to indicate that the stress level of an individual has been mitigated by being reduced to a level sufficient to indicate relief from stress. The bi-lateral stimulation applied may be programmed by the individual (as will be discussed below in connection with FIGS. 10-14) or optionally may have an initial therapy Th1 906 programmed into the memory table 808 which may be selected to correspond with the parameter 900 exceeding the threshold 902. Additionally, in some embodiments, a modified therapy MTh1 908 can also be programmed into memory table 808. In the event that the initial therapy does not mitigate the detected stress, the modified therapy may be initiated to attempt to achieve mitigation or at least some reduction in stress. As will be appreciated, the modified therapy may vary from parameter to parameter (P1-PN) and may be a change in intensity, duration or overlap period (see FIGS. 15A-C and FIG. 16).

In some embodiments, the mitigation value M1 904 may be selected to be a certain percentage (e.g., 5%) below the threshold value 902. That is, mitigation of a detected stressful event (and thus the cessation of bi-lateral stimulation) may be achieved by reducing the measured response of a parameter P1 900 beyond the level indicated by threshold value T1 to a mitigation value M1 904 selected to assure that the individuals stress response has been mitigated. In other embodiments, the mitigation value M1 904 may be selected to be a certain percentage below the current measured physiological parameter determined by the processor to indicate stress (or the onset of stress).

As noted above, in some embodiments, the values P1-PN, T1-TN, M1-MN, Th1-ThN and MTh1-MThN are entered as default values or may be programmed into the memory table 808 by a stress therapist or other stress response medical professional. Thereafter, the values may be updated based upon machine learning of the physiological and environmental parameters determined by the processor and the person's response to the application of bi-lateral stimulation. Accordingly, in some embodiments the processor analyzes the measured physiological environmental parameters prior to and after bi-lateral stimulation to determine whether a new event has occurred such that the stimulation model and parameters of memory table 808 would benefit by retraining (updating) the stimulation model for future applications of bi-lateral stimulation as will be discussed below in connection with FIG. 19.

The new event function attempts to retrain machine learning model based upon newly measured physiological and environmental parameters from the person as well as the person's response to the application of bi-lateral stimulation. Initially, the algorithm checks to see if the event is learnable and then applies a classifier label for the new event data. Next a new training vector is normalized and then used to train a new stimulation model. Before being pushed (transmitted) to the mobile device 102, the new model is cross validated to ensure classification accuracy. The new model may be cross validated as not deviating by more than a certain percentage from the prior classification or against statistically averaged multi-person population data.

```
Function: new_event( )
Input: event, new_data, previous_data
Output: new_classifier_model
    Variable label // label for new training vector
    Variable newTrainingVector
    Variable new_classifier_model
    If event is in learnable_list
        label = get_label(event, new_data)
        newTrainingVector = build_normailzed_vector(label,
            new_data)
        If cross_validate(newTrainingVector, previous data) =
            TRUE
            new_classifier_model = train_classifier
                (new_data, previous_data)
            push_new_model(new_classifier_model)
```

Non-limiting examples of parameters that may indicate a new event for retraining the stimulation model include, but are not limited to, heart rate variability, blood oximetry, humidity, barometric pressure, ambient temperature, skin temperature, or accelerometer readings from an inertial measurement unit. In this way, machine learning via the cloud may be used to more finely tune each person's bilateral stimulation app to more effectively help the person reduce stress and improve performance.

As will be discussed in detail below, in some exemplary embodiments, multiple parameters from multiple sensors are used to confirm or dispel a stressful event or situation. That is, when sensor data from one sensor indicates the appearance of stress, parameters from other sensors (physiological and environmental) are analyzed by the processor prior to initiating bi-lateral stimulation.

As a first non-limiting example, if heart rate (sensor 214) where to exceed its parameter threshold and skin temperature (sensor 224) where to exceed its threshold, the processor 802 may determine not to initiate bi-lateral stimulation as the individual may simply be exercising. Conversely, rising heart rate and steady or falling skin temperature, may indicate the onset on stress causing the processor 802 to begin an initial therapy from the memory table 808. Another sensor data verification example to not simulate for simple activity would be if heart rate (sensor 214) where to exceed its parameter threshold and one or both of the acceleration parameters (sensors 226, 230) indicated motion in excess of their respective thresholds, the processor 802 may determine not to initiate bi-lateral stimulation.

As another non-limiting example, if skin temperature (sensor 224) exceeded (fell below) its threshold and ambient temperature (sensor 234) was falling, the processor 802 may determine not to initiate bi-lateral stimulation as the individual may simply have entered in a cold environment.

Yet another non-limiting example would be if the blood pressure (sensor 216) parameter exceeded its threshold, but the blood oxygen (sensor 220) parameter or air quality (sensor 240) parameter did not exceed their respective thresholds then the processor 802 may determine not to initiate bi-lateral stimulation.

As will be appreciated by those skilled in the stress therapy arts, various combinations of the multiple sensors and programmed thresholds may be used to detect and apply (or determine to not apply) bi-lateral stimulation depending upon the programmed values in the memory table 808.

Figure 10:
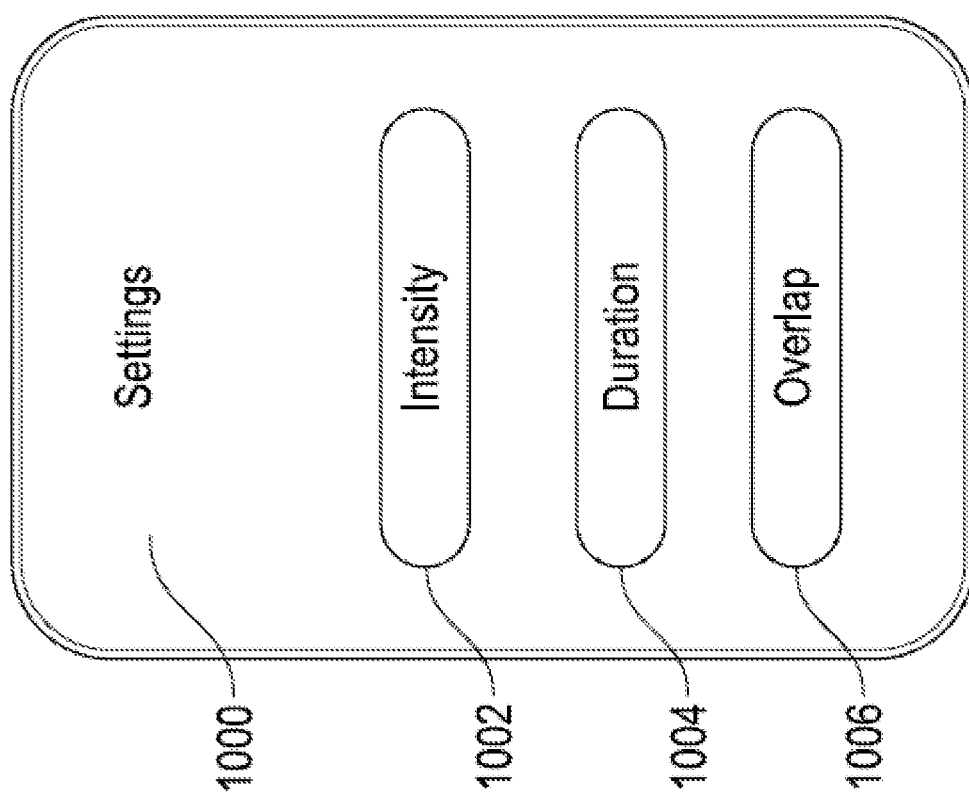
FIG. 10 is an illustration of a mobile device screen-shot for programming the stimulation applied by the stimulation elements in accordance with non-limiting embodiments.

FIGS. 10-14, are non-limiting illustrations of a display screen of the mobile device 102 that may be used to program the alternating asynchronous bi-lateral stimulation of the bi-lateral stimulation system 100. In FIG. 10, a settings screen 1000 is illustrated having a touch-sensitive button 1002 to adjust the intensity of the vibrations, a button 1004 to adjust the speed of the vibrations and a button 1006 to adjust the overlap period during which both vibrating elements 104 are simultaneously applying stimulation to an individual's body. If no settings are provided (programmed) by the individual, the continuous bi-lateral stimulation mode is selected, with constant intensity and speed over the stimulation time periods.

Figure 11:
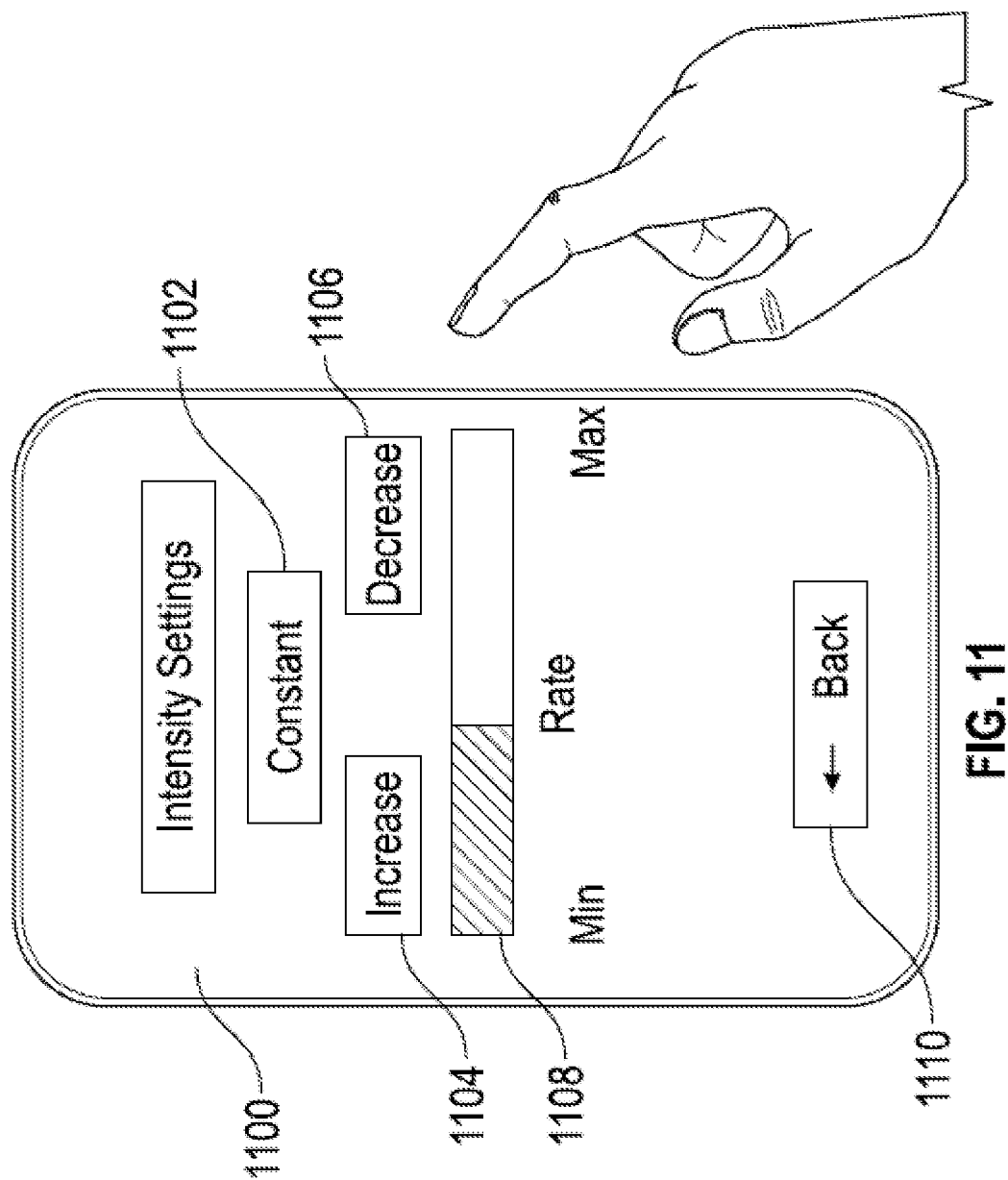
FIGS. 11-14 are illustrations of programming one parameter of the stimulation elements in accordance with a non-limiting embodiment.

FIG. 11 illustrates an example where the intensity button 1002 has been activated by the individual. According to exemplary embodiments, the intensity of stimulation during the stimulation time period may be constant, gradually increasing or gradually decreasing. Accordingly, the intensity setting screen 1100 include selection buttons for selecting (programming) constant 1102, increasing 1104 or decreasing 1106 stimulation. In one non-limiting embodiment, when a user selects either the increasing button 1104 or the decreasing button 1106, a slide-bar adjustment area 1108 become active so that the individual may drag an indicator from a minimum ("Min") setting to a maximum ("Max") setting as shown. Additionally, the intensity settings screen 1100 presents individual with a touch-sensitive back button 1110 to return to the setting screen 1000 of FIG. 10.

Figure 12:
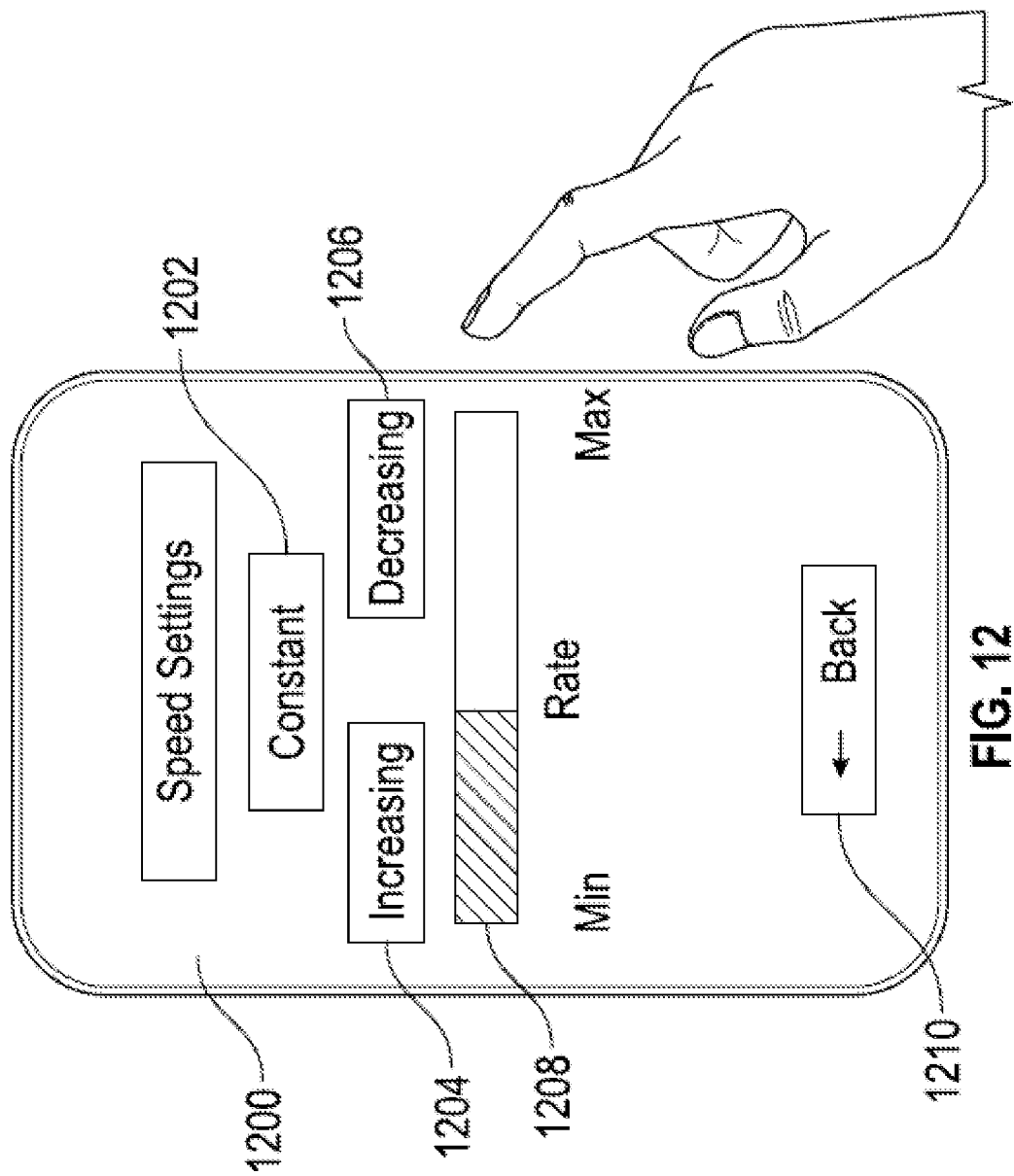

FIG. 12 illustrates an example where the speed button 1004 has been activated by the individual. According to exemplary embodiments, the speed that the stimulation is applied during the stimulation time period may be constant, gradually increasing or gradually decreasing. Accordingly, the speed setting screen 1200 include selection buttons for selecting (programming) constant 1202, increasing 1204 or decreasing 1206 stimulation speed. In one non-limiting embodiment, when a user selects either the increasing button 1204 or the decreasing button 1206, a slide-bar adjustment area 1208 become active so that the individual may drag an indicator from a minimum ("Min") setting to a maximum ("Max") setting as shown. Additionally, the speed settings screen 1200 presents individual with a touch-sensitive back button 1210 to return to the setting screen 1000 of FIG. 10.

Figure 13:
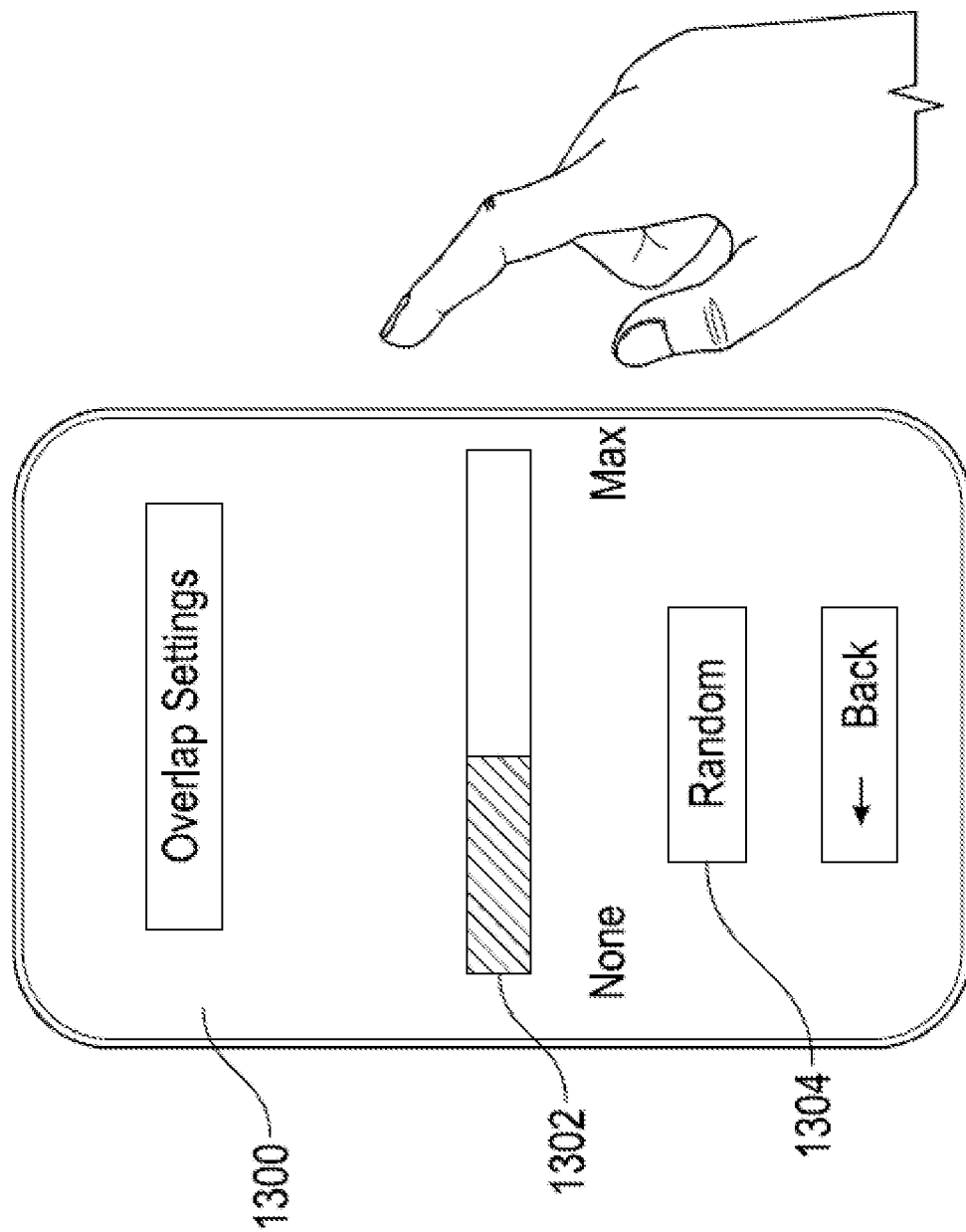
Figure 14:
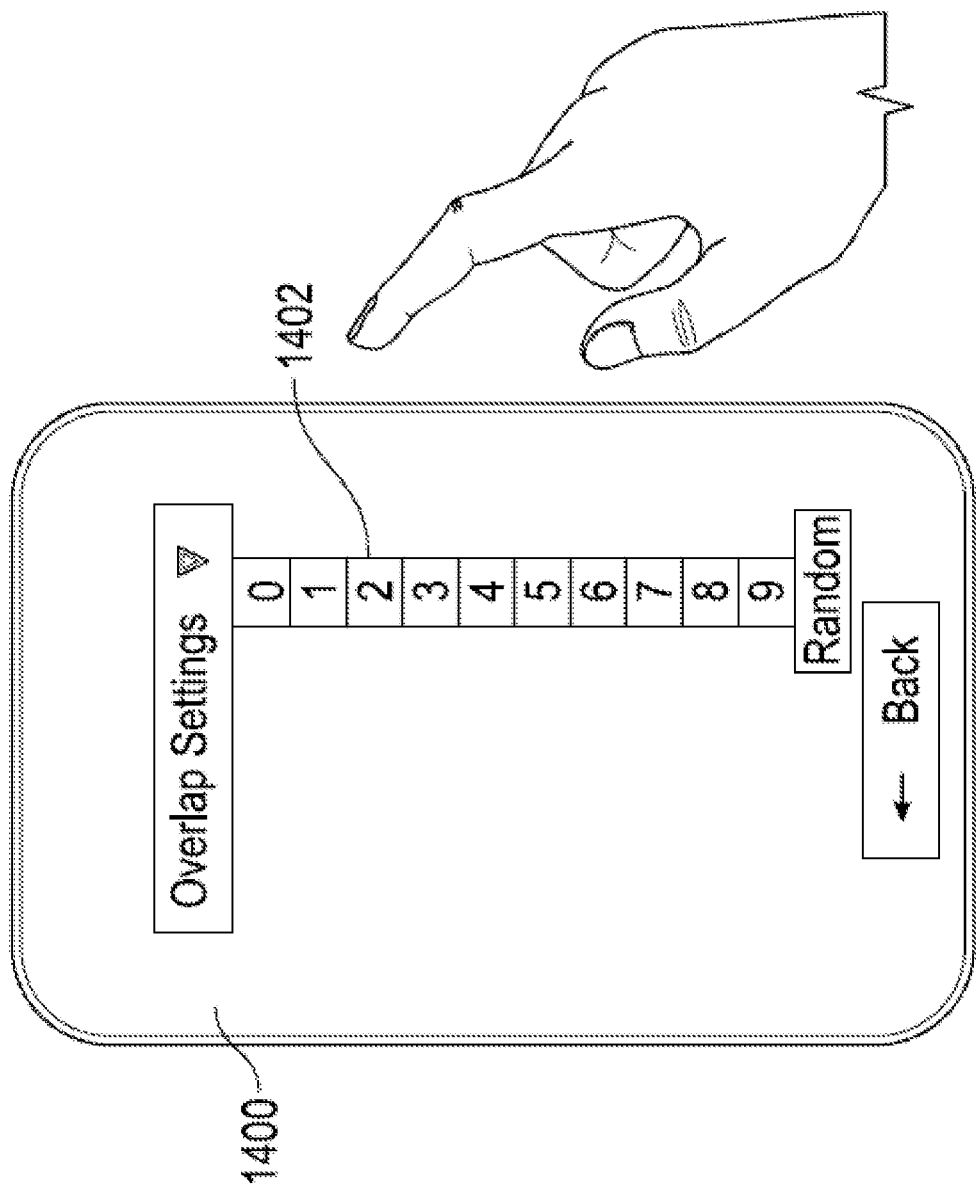

FIG. 13 illustrates an example where the overlap button 1006 has been activated by the individual. In one non-limiting embodiment, the overlap settings screen 1300 includes a slide-bar adjustment area 1302 so that the individual may drag an indicator from a "none" setting (continuous bi-lateral stimulation mode) to a "maximum" overlap setting as shown. Additionally, the overlap settings screen 1300 presents individual with a touch-sensitive randomize button 1304. When the randomize button 1304 is selected by the individual, the time period in which both vibrating elements 104 (or vibrating arrays) simultaneously vibrate is randomly selected by the controller (202 of FIG. 2) as will be discussed below. In FIG. 14, an alternate non-limiting embodiment of an overlap settings screen 1400 is illustrated having a drop-down menu 1402 in which the period of overlap ("0" being the continuous bi-lateral stimulation mode), or the random setting, may be selected by the individual. As will be appreciated by those skilled in the art, the screen format illustrated in FIG. 14 may also be used for adjusting the intensity setting (FIG. 11) and the speed setting (FIG. 12).

FIGS. 15A-15B are timing diagrams illustrating non-limiting embodiments of the alternating asynchronous bi-lateral stimulation as contemplated by the present disclosure. In FIG. 15A, a timing diagram 1500 illustrates a time period 1502 during which one of the vibrating elements 104 (designated "R" for a right side of an individual's body) is vibrating. Timing diagram 1500 also includes a time period 1504 during which the opposite side (designated "L" for a left side of an individual's body) vibrating element 104 is vibrating. An overlap time period 1506 is also illustrated during which both vibrating elements 104 are simultaneously vibrating. In the embodiment of FIG. 15A, the duration of the overlap period 1506 is programmed by the individual in any suitable manner, including the non-limiting examples provided in connection with FIGS. 13-14. In FIG. 15B, the randomize option has been selected by the individual (see 1304 of FIG. 13) which causes the time period in which both vibrating elements are simultaneously vibrating to be randomly selected between vibrating cycles from one side of the individual's body to the bi-lateral (opposite) side. As an example, and not as a limitation, observing from the left-side to the right-side of FIG. 15B shows a leading-edge (meaning the beginning of the vibration period 1504) 1508 beginning at the maximum point (most amount of simultaneous vibration) of the overlap time period 1506. The leading-edge 1508' of time period 1502 can be seen to have a shorter time of overlapping vibrations. Moving on, leading-edge 1508" of time period 1504 can be seen to begin at about the midpoint of the overlap time period 1506. In the embodiment illustrated by timing diagram 1500' the alternating vibrations would continue to randomly overlap within the overlap time period 1506 until the individual deactivates the vibrating elements by controlling the mobile device 102.

Figure 15C:
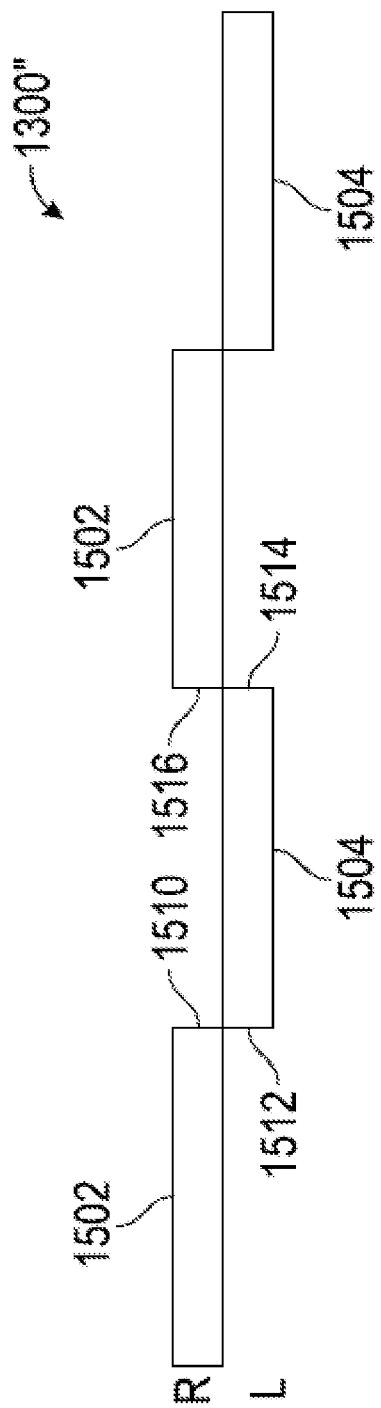

FIG. 15C is a timing diagram illustrating non-limiting embodiments of the alternating continuous bi-lateral stimulation as contemplated by the present disclosure. In FIG. 15C, a timing diagram 1500" illustrates a time period 1502 during which one of the vibrating elements 104 (designated "R" for a right side of an individual's body) is vibrating. Timing diagram 1500 also includes a time period 1504 during which the opposite side (designated "L" for a left side of an individual's body) vibrating element 104 is vibrating. As illustrated in FIG. 15C, at the conclusion (trailing edge 1510) of the vibrating time period 1502, the vibrating period 1504 begins (leading edge 1512) without pause or interruption in the stimulation being applied to the individual. As such, this form of stimulation is said to be continuous bi-lateral stimulation. Similarly, at the conclusion (trailing edge 1514) of the vibrating time period 1504, the vibrating period 1502 begins again (leading edge 1516) also without pause or interruption in the stimulation being applied to the individual.

Figure 16:
FIG. 16 are illustrations of various permutations of operating modes of the present disclosure in accordance with non-limiting embodiments.

FIG. 16 illustrates some of the possible operating modes of the system of the present disclosure to provide the therapeutic benefit afforded by the method disclosed herein. As discussed above in connection with FIGS. 15A-15C, one mode of operation focuses on whether the system is providing alternating asynchronous bi-lateral stimulation (fixed or random overlap) or alternating continuous bi-lateral stimulation (no gap or pause between left and right stimulations). Additionally, as shown in FIG. 16, the intensity and the speed of stimulation may be constant, gradually increasing or gradually decreasing over the stimulation period leading to the nine operating modes illustrated in FIG. 16. A person can vary the settings (see, FIGS. 10-14 and associated text) to find the mode of operation that provides the greatest benefit to that person under the present circumstances.

Figure 17:
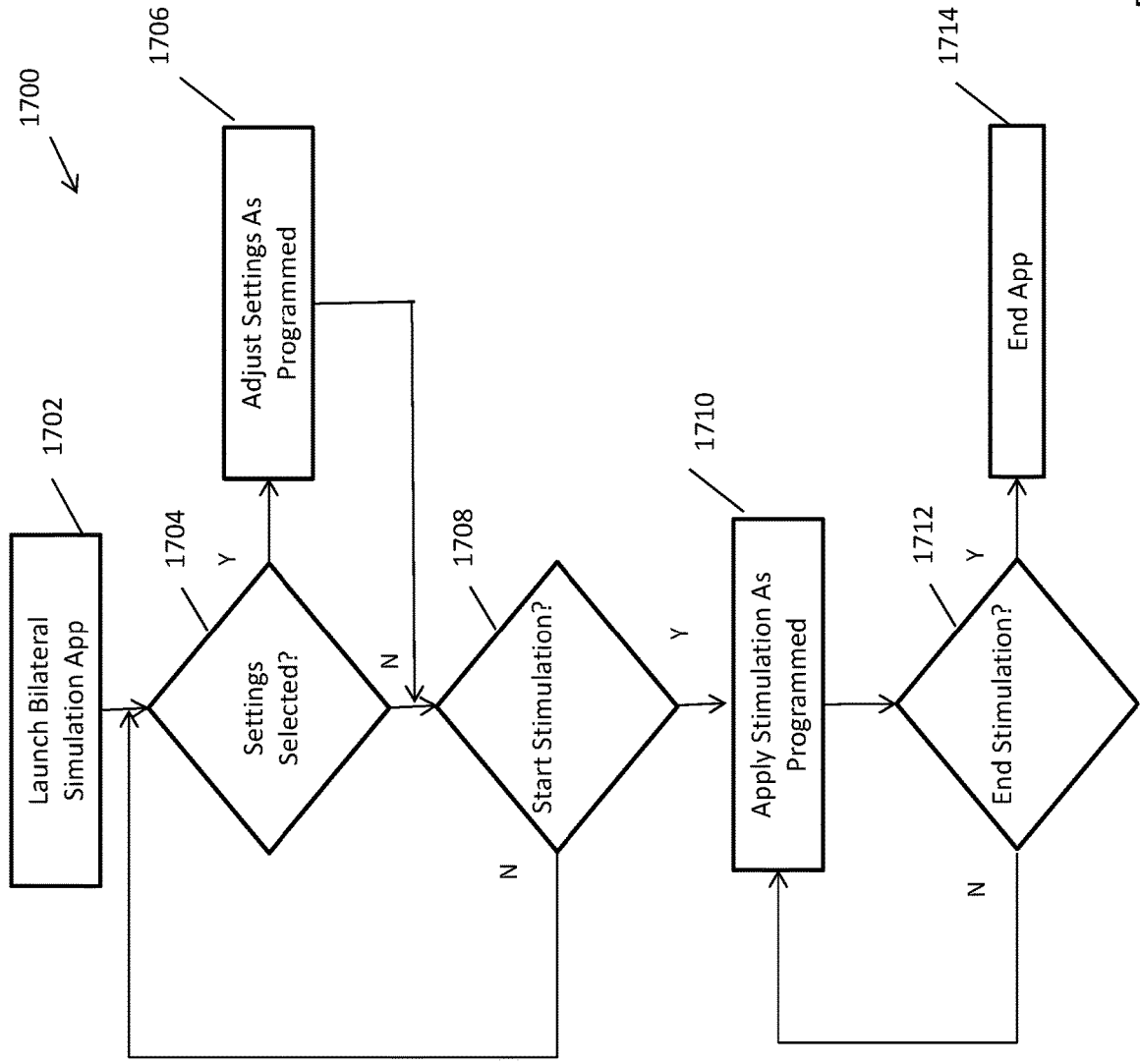
FIG. 17 is a flowchart of a manual bi-lateral stimulation method in accordance with a non-limiting embodiment.

FIG. 17 is a flow diagram of a method 1700 performed by the bi-lateral stimulation system for manual application of bi-lateral stimulation in accordance with a non-limiting embodiment. In one embodiment, the various tasks performed in connection with the method 1700 of FIG. 17 are performed by instruction stored on a non-transitory computer medium (e.g., application program 806 of FIG. 8) being executed in a processing unit (e.g., processor 802 of FIG. 8), hardware, firmware, or any combination thereof.

For illustrative purposes, the following description of the method 1700 of FIG. 17 refers to elements mentioned above in connection with FIG. 1 to FIG. 16.

It should be appreciated that the method of FIG. 17 may include additional or alternative tasks or may include any number of additional or alternative tasks, and that the method of FIG. 17 may be incorporated into a more comprehensive procedure or process having additional functionality not described in detail herein or implemented as a stand-alone procedure. Moreover, one or more of the tasks shown in FIG. 17 are removable from an embodiment of the method 1700 of FIG. 17 as long as the intended overall functionality remains intact.

The method begins in block 1702 where the bi-lateral stimulation application (app) is launched (begun) on the mobile device 102 so that the individual may receive the asynchronous (or continuous) alternating bi-lateral stimulation as discussed above. In block 1704, a determination is made as to whether the individual has selected a settings feature to adjust the programming of the stimulation as discussed above in connection with FIGS. 10-14. If the determination of block 1704 is that the individual has elected to adjust the programming of the stimulation, the method proceeds to block 1706 where the settings are adjusted as desired by the individual as discussed above. Conversely, if the determination of block 1704 is that the individual has not elected to change the stimulation programming, the routine proceeds to block 1708 to determine whether the individual has activated the stimulation. If not, the routine loops around to block 1704 and routine continues. Assuming the determination of block 1708 is that the individual desires to commence stimulation, the stimulation is applied in asynchronous (or continuous) and alternate manner in block 1710 as discussed above. The stimulation can continue for a time period of until the individual decides to stop the stimulation as determined in block 1712, at which point the application ends in block 1714. Otherwise, the routine loops back to step 1710 and the stimulation is continued for a predetermined time period or for any time period desired by the individual.

Figure 18A:
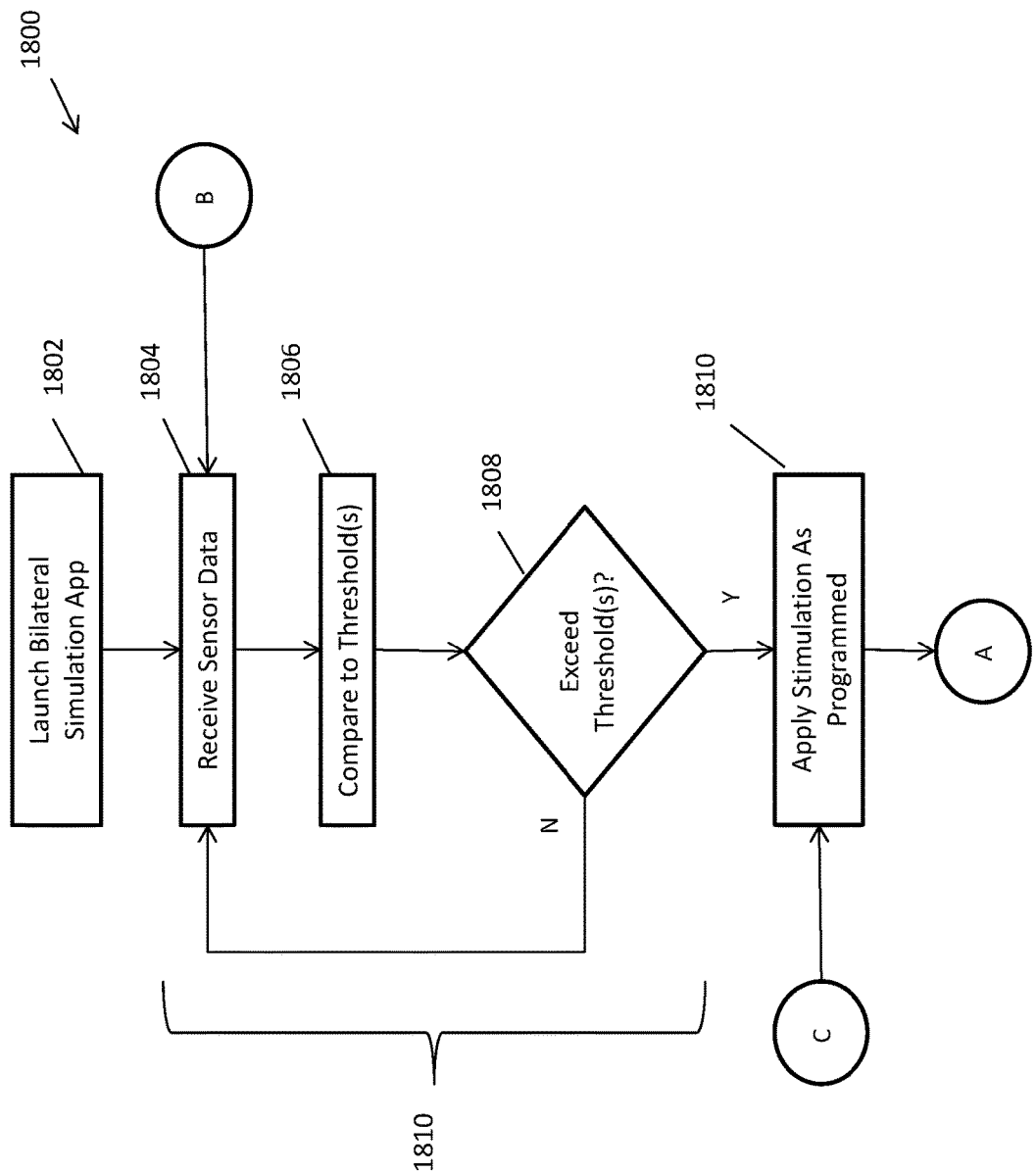
FIGS. 18A-18F are flow charts of an automatic (closed-loop) bi-lateral stimulation method in accordance with non-limiting embodiments.
Figure 18B:
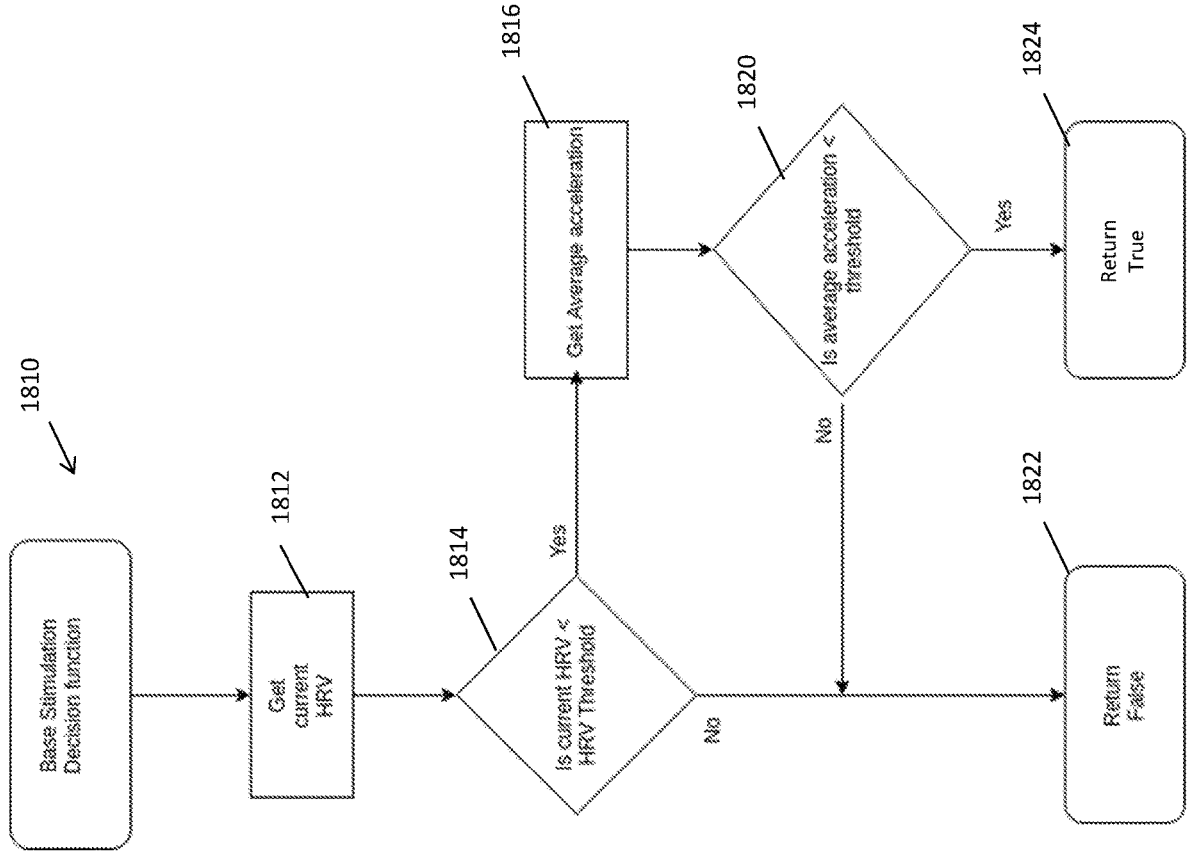
Figure 18C:
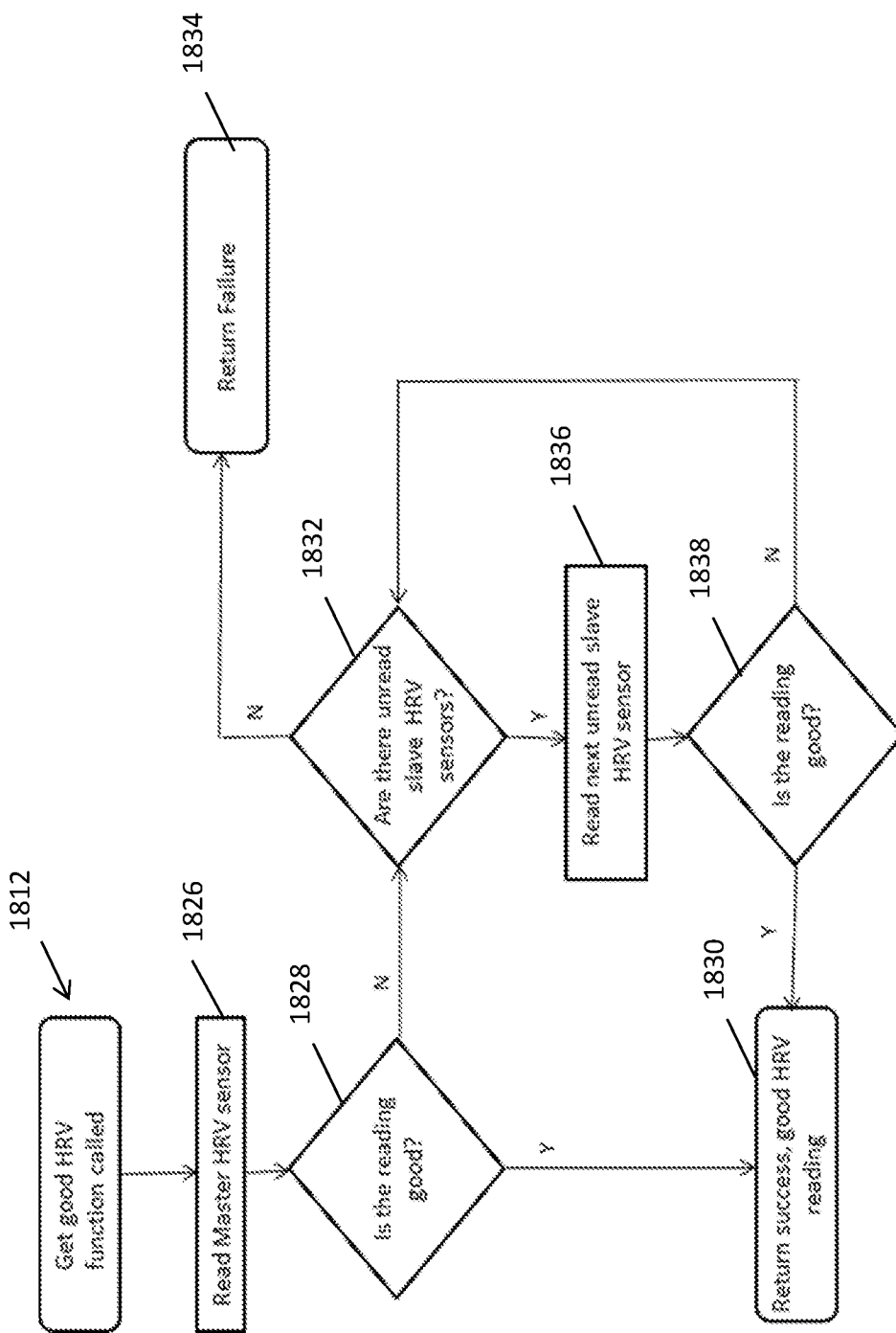

FIGS. 18A-18C are flow diagrams of a method 1800 performed by the bi-lateral stimulation system for automatic (closed-loop) application of bi-lateral stimulation in accordance with a non-limiting embodiment. In one embodiment, the various tasks performed in connection with the method 1800 of FIGS. 18A-C are performed by instruction stored on a non-transitory computer medium (e.g., application program 806 of FIG. 8) being executed in a processing unit (e.g., processor 802 of FIG. 8), hardware, firmware, or any combination thereof.

For illustrative purposes, the following description of the method 1800 of FIGS. 18A-C refers to elements mentioned above in connection with FIG. 1 to FIG. 16.

It should be appreciated that the method 1800 of FIGS. 18A-C may include additional or alternative tasks, or may include any number of additional or alternative tasks, and that the method of FIGS. 18A-C may be incorporated into a more comprehensive procedure or process having additional functionality not described in detail herein or implemented as a stand-alone procedure. Moreover, one or more of the tasks shown in FIGS. 18A-C are removable from an embodiment of the method 1800 of FIGS. 18A-C as long as the intended overall functionality remains intact.

In fundamental embodiments, the basic routine determines whether therapy should be initiated by detecting stress (or the onset stress) in a person and then determining if the stress has been mitigated after the provision of therapy. If not, a modified therapy can be applied after which the routine again determines whether the stress has been mitigated. This main decision loop can be repeated any number of times as desired any particular implementation, and may be expressed in code as follows:

```
Main Decision Function
   variable sleeptime = 30 seconds
   while (not quit):
      if stimulation_decision( ):
         execute_initial_tharapy( ):
         if not stimulation_evaluation( ):
            execture_modified_therapy( ):
            if not stimulation_evaluation( ):
               sleep(sleeptime)
```

In the interest of brevity, the following non-limiting example will utilize heart rate variability and the accelerometer reading to determine the onset of stress. However, it will be appreciated that any combination of sensor readings (see FIG. 3 and FIG. 4) maybe used to determine the onset of stress. Additionally, within the sensors selected for evaluation one or more sensors (i.e., master sensor or master and one or more slaves sensors) positioned on the person (see FIG. 5C) maybe used as desired any particular implementation.

Referring now to FIG. 18A, the method begins in block 1802 where the bi-lateral stimulation application (app) is launched (begun) on the mobile device 102 so that the individual may receive the asynchronous (or continuous) alternating bi-lateral stimulation in an automatic (closed-loop) mode as discussed above. In block 1804, the mobile device (e.g., processor 802) receives the sensor data from the physiological sensors 210 and the environmental sensors 212. In block 1806, the receive sensor data is compared to thresholds stored in the memory table (e.g., 808 of FIG. 8) in block 1808 determines whether any of the received sensor parameter data exceeds the threshold. Blocks 1804, 1806 and 1808 may be referred to as a base stimulation decision function 1811 for the bi-lateral stimulation application. In the example presented of heart rate variability in accelerometer this may be accomplished as illustrated in FIG. 18B.

In FIG. 18B, to execute the base stimulation decision function 1811, the processor first determines a current heart rate variability (HRV) in block 1812 from receive sensor data. This example will be shown in more detail in FIG. 18C below. Next block 1814 determines if the current HRV is less than the HRV threshold, and if so, block 1816 determines the average acceleration to determine if the person is in motion, which may indicate activity but not the presence of stress. Block 1820 compares the average acceleration to a threshold and determines if the average acceleration is less than the threshold. If so, the routine returns true (meaning stimulation should commence) in block 1824 and if not (or if the outcome of block 1814 is negative), the routine returns false in block 1822 (meaning stimulation should not commence).

To determine the HRV threshold, the routine may look to a value stored in the memory table of FIG. 9. Or, as an initial condition, the HRV threshold may be computed by obtaining multiple HRV measurements over the course of time interval recording the highest and lowest HRV values determined this may be expressed in code as follows:

```
Function to Get HRV Threshold
Function: get_HRV_threshold( ):
Input: baselineDuration in seconds
Ouput: HRV threshold value
   variable HRV/Max // initialize to a low value
   variable HRV/Min // initialize to high value
   variable HRVMean = 0.0
   variable HRVSum = 0.0
   variable baselineDuration = 20.0 /* Minutes */
   variable currentHRV = 0.0
   variable numSamples = 0
   variable startTime = getTime( )
   while ((getTime( ) - startTime) < baselineDuration
      numSamples = numSamples + 1
      currentHRV = get_good_HRV( )
      HRVSum = HRVSum + currentHRV
      If currentHRV > HRT/Max:
         HRV/Max = currentHRV
      If currentHRV < HRVMin:
         HRVMin = currentHRV
   HRVMean = HRVSum / numSamples
   return HRV/Min - ((HRV/Mean - HRV/Min) / 2)
```

In a similar manner, the accelerometer threshold may be retrieved from the memory table of FIG. 9, or as an initial condition, may be determined by calculating a baseline acceleration value for an accelerometer axis and returning the threshold value. This can be implemented by calculating maximum, minimum and means values and then returning a threshold value that is the maximum value plus half the distance between the maximum and mean values. This can be expressed in code as follows:

```
Function to Get Accelerometer Threshold
Function get_ACC_threshold( ):
   variable ACCMax /* initialize to a low value */
   variable ACCMin /* initialize to high value */
   variable ACCMean
   variable ACCSum
   variable baselineDuration = 5.0 /* Minutes */
   variable currentACC
   variable numSamples
   variable startTime = getTime( )
   while ((getTime( ) - startTime) < baselineDuration:
   numSamples = numSamples + 1
      currentACC = get_ACC()
      ACCSum = ACCSum + currentACC
      If currentACC > ACCMax:
         ACCMax = currentACC
```

```
    If currentACC < ACCMin:
        ACCMin = currentACC
    ACCMean = ACCSum / numSamples
    return ACCMax + ((ACCMax - ACCMean) / 2) // returns 25%
    above max value
```

Referring now to FIG. 18C, block 1812 of FIG. 18B can be expressed in more detail utilizing the example of having one or more slaves sensors positioned at various places in the person (see FIG. 5C). In block 1826, a master HRV sensor provides data to the processor 802. Block 1828 determines whether they sensor reading was valid. In some embodiments, the processor 802 may execute a moving average valuation on HRV sensor readings over a time interval to counteract the presence of noise in the sensor readings. This moving average function may be expressed in code as follows:

```
Moving Average Function
Function get_moving_average(last_average, current_reading, alpha)
    variable current_moving_average
    current_moving_average = alpha * currrent_reading + (1 - alpha) *
    last_average
    return current_moving_average
```

If the determination of block 1828 is at the master HRV sensor reading is valid, the master sensor HRV reading is returned in block 1830. However, if the determination of decision 1828 that the master sensor reading is not valid, the function proceeds to block 1832 determines whether there are any unread slave HRV sensors present on the person. If not, block 1834 returns a failure flag which causes the mobile device 102 to indicate a system failure to the user. However, assuming there are unread slave sensors available block 1836 reads the next unread slave HRV sensor and decision 1838 determines if that reading is valid. If not, the routine loops back to block 1832 until all slave sensors readings have been exhausted. In some embodiments, a master and/or multiple slaves sensor readings that have varying degrees of noise may be combined in order to obtain a good reading. To do this, a Kalman filter function may be employed to provide the sensor reading combining function. This may be expressed in code as follows:

```
Kalman Filter Function
Function kalman_filter( ):
    Input: last state vector estimate sv_last, state covariance estimate
    P_last, vector uv, Measurement vector zv
    Output: state vector estimate sve, state covariance estimate Pe
        constant A //state matrix
        constant B //sensor input matrix
        constant H //measurement matrix
        constant Q //noise covariance matrix
        constant I // Identity matrix
        variable sv //state vector
        variable sve //state vector estimate
        variable P //state covariance matrix
        variable Pe //state covariance matrix estimate
        variable K //Kalman gain
        variable zve //measurement vector estimate
        sv = A * sv_last + B * uv
        P = A * P_last * transpose(A) + Q
        K = P * transpose(H) * inverse(H * P * transpose(H) + Q)
        ze = (zv - H * sv)
        sve = sv + K * zve
        Pe = (I - K * H) * P
        return sve, Pe
```

Returning again to FIG. 18A, if the determination of block 1808 is that stimulation should be not provided to the person, the routine loops back to block 1804 to await the reception of the next package of sensor data which may occur periodically (e.g., every minute, 5 minutes, 10 minutes) or as desired in any particular implementation. If one or more of the thresholds has been exceeded, block 1810 applies alternating bi-lateral stimulation as programmed. In some embodiments, the programming represents the bi-lateral stimulation as programmed by the individual for the manual mode (see FIGS. 10-14). In other embodiments, the programming represents a bi-lateral stimulation programming associated with the sensor parameter parameter(s) that have exceeded their threshold (e.g., Th1 of FIG. 9). After the stimulation has been applied by block 1810 (for example after a time period or as a stimulation therapy session is about to conclude) the mobile device 102 receives refreshed/updated sensor data in block 1812.

Figure 18D:
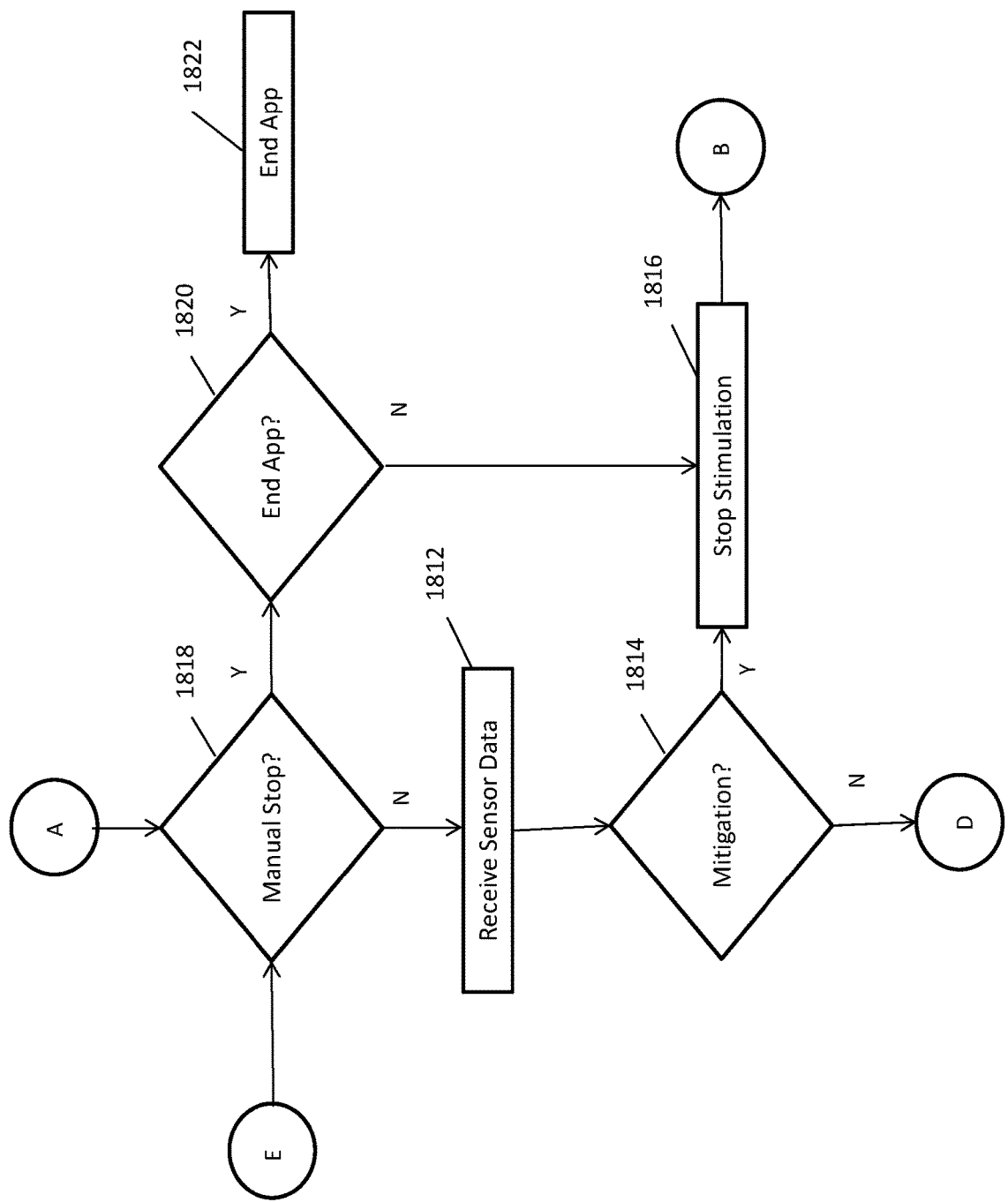

Continuing with reference to FIG. 18D, after block 1810 begins the initial therapy, block 1818 determines whether a manual stop command has been entered by the user. If so, then it is possible that the bi-lateral stimulation app is incorrectly determined the onset of a stressful condition. For example, if an individual had engaged in an outdoor activity, but was not under stress, it is possible that the bi-lateral stimulation app (806 in FIG. 8) may have incorrectly determined that a stressful condition had occurred (or was about to occur) for the individual. Alternately, it could be that the individual is experiencing stress, however, it may not be a convenient time for the person to receive alternating bi-lateral stimulation therapy. Accordingly, if block 1818 determines that a manual stop command was received, block 1820 determines whether the individual has instructed the bi-lateral stimulation app to end so that the individual may continue with the activity that s/he is engaged in without further automatically triggering further bi-lateral stimulation. If so, the app ends in block 1822, otherwise the stimulation is simply stopped in block 1816 the routine returns back to block 1804 for the next cycle of updated sensor data.

If a manual stop command was not received, block 1812 receives updated sensor data and block 1814 determines if mitigation of the stress has been achieved. In some embodiments, the mitigation of stress is determined by the sensor parameter equaling or falling below the mitigation threshold (e.g., M1 of FIG. 9) as discussed above. In other embodiments, mitigation of stress may be determined by the sensor parameter falling below the threshold that triggered the application of the bi-lateral stimulation (e.g., T1 of FIG. 9), as illustrated in FIG. 18E.

Figure 18E:
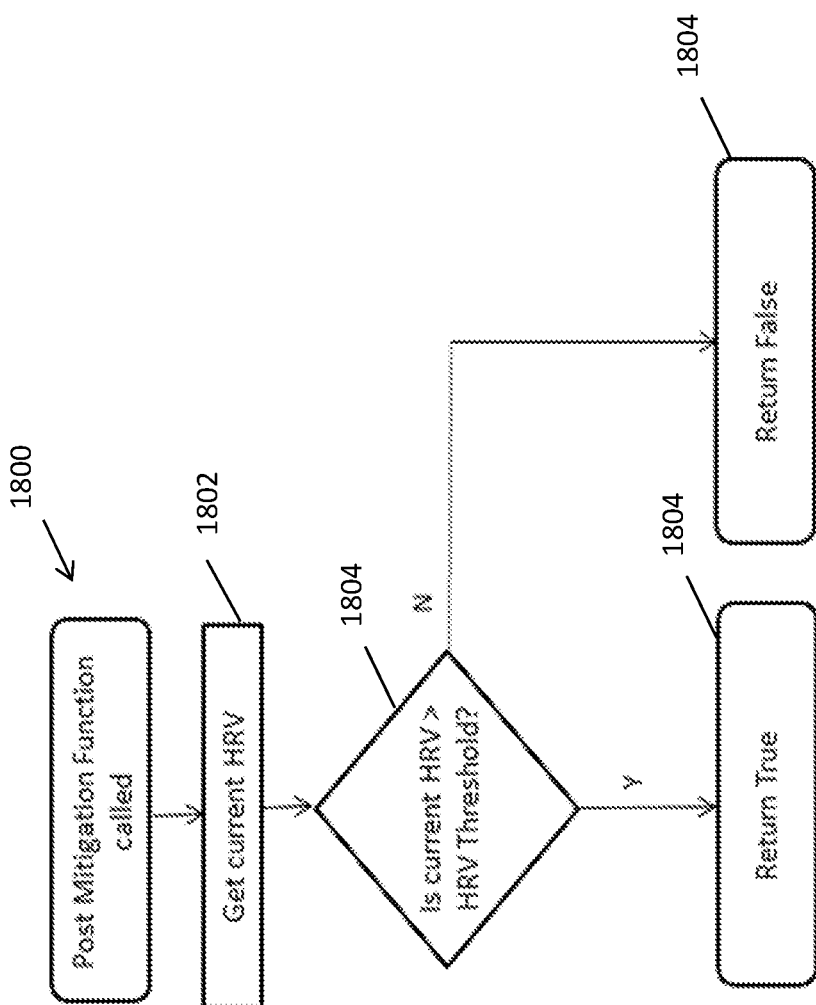
Figure 18F:
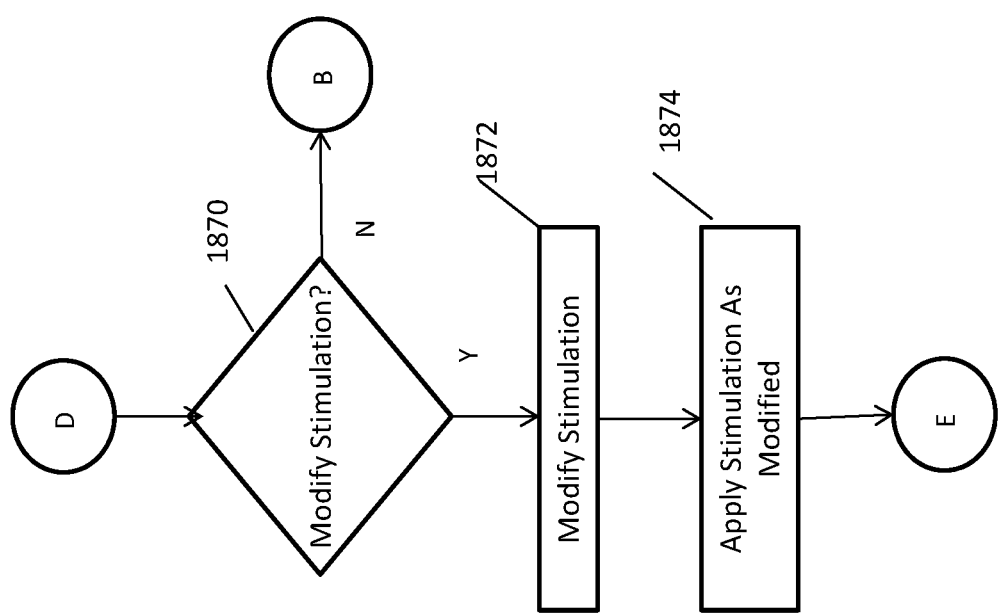

In FIG. 18E, the processor 802 calls a post stimulation function 1860 which begins by getting the current HRV value in block 1862. Next block 1864 determines whether the current HR be reading is above the HRV threshold that was used to trigger the application of stimulation. If the current HR a reading is above the threshold, a true value is returned in block 1866 (meaning that mitigation has been achieved), otherwise a false flag is returned in block 1868. This function/algorithm can be expressed in code as follows:

```
Post Stimulation Function
Function stimulation_evaluation( ): /* True if stimulation worked */
    variable HRV_threshold = get_post_HRV_threshold( )
```

```
If get_current HRV( ) > HRV_threshold:
    return TRUE
else:
    return FALSE
```

If mitigation has been achieved, then the stimulation is stopped in block 1816 and the routine returns to block 1804 two receive the next cycle of updated sensor information. Conversely, if the determination of block is that mitigation has not been achieved, the routine continues in FIG. 18F where block 1870 determines whether to modify the bi-lateral stimulation being applied. As will be appreciated, at this point in the routine, bi-lateral stimulation has been provided (block 1810) but mitigation has not occurred (block 1850). Therefore, block 1870 determines whether to modify the stimulation being applied. Non-limiting examples of modification include increasing intensity, increasing duration, changing the stimulation overlap period, changing from continuous to asynchronous bi-lateral stimulation or any other modifications desired in any particular implementation (see FIG. 16). If the determination of block 1870 is that no modification is needed, the routine loops back to block 1804 where the routine continues to receive the sensor data. Conversely, if the determination of block 1870 is to modify the bi-lateral stimulation, that modification is implemented in block 1872 in the stimulation is applied in block 1874 before returning to block 1818 to determine whether the user has manually terminated the modified bi-lateral stimulation. In this way, the present disclosure improves an individual's performance by a reduction in stress that can assist a person in real or imagined stressful situations in everyday life or to relieve stress or anxiety prior to surgery or a medical procedure (for themselves or a family member), relieve post-surgical and physical therapy stress during recovery.

As noted above, in some embodiments, the values P1-PN, T1-TN, M1-MN, Th1-ThN and MTh1-MThN are entered as default values or may be programmed into the memory table 808 by a stress therapist or other stress response medical professional. Thereafter, the values may be updated based upon machine learning of the physiological and environmental parameters determined by the processor and the person's response to the application of bi-lateral stimulation. Accordingly, in some embodiments the processor analyzes the measured physiological environmental parameters prior to and after bi-lateral stimulation to determine whether a new event has occurred such that the stimulation model and parameters of memory table 808 would benefit by retraining (updating) the stimulation model for future applications of bi-lateral stimulation as will be discussed below in connection with FIG. 19. The new event function attempts to retrain machine learning model based upon newly measured physiological and environmental parameters from the person as well as the person's response to the application of bi-lateral stimulation. Initially, the function/algorithm checks to see if the event is learnable and then applies a classifier label for the new event data. Next a new training vector is normalized and then used to train a new stimulation model. Before being pushed (transmitted) to the mobile device 102, the new model is cross validated to ensure classification accuracy. The new model may be cross validated as not deviating by more than a certain percentage from the prior classification or against statistically averaged multi-person population data.

Figure 19:
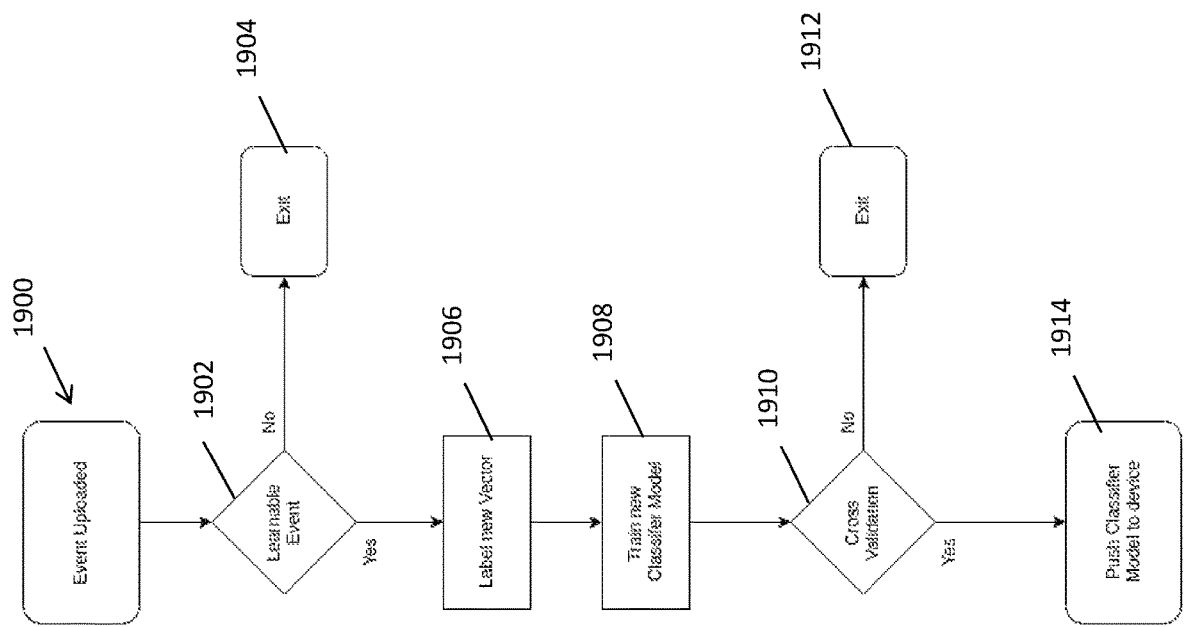
FIG. 19 is a flow chart of a machine learning function in accordance with non-limiting embodiments.

Referring now to FIG. 19, a non-limiting example routine for achieving retraining of the stimulation model is shown. The routine begins in block 1900 after a new event has been uploaded to determine if the event should be used for retraining of the stimulation model. Block 1902 determines whether the event is learnable and if not the routine exits in block 1904. However if the event is learnable a new vector label is collected and applied to the event in block 1906 and it is used to retrain the stimulation classifier model in block 1908. Block 1910 determines whether the newly trained stimulation model has passed cross validation, and if not, the routine exits in block 1912. Conversely, if cross validation is successful block 1910 which is the new classifier model to the mobile device 102 in block 1914. The cross validation tests how well the data set with the new added data, will generalize to predict data not yet seen as in for example, a new stress state. If the new data makes generalization worse, the new data is discarded. As one non-limiting example, the new event machine learning function can be expressed in code as follows:

```
New Event Machine Learning Function
Function: new_event( )
Input: event, new_data, previous_data
Output: new_classifier_model
    Variable label // label for new training vector
    Variable newTrainingVector
    Variable new_classifier_model
    If event is in learnable_list
        label = get_label(event, new_data)
        newTrainingVector = build_normailzed_vector(label,
            new_data)
        If cross_validate(newTraingVector, previous_data) = TRUE
            new_classifier_model = train_classifier (newTrainingVector,
                previous data)
            push_new_model(new_classifier_model)
```

Non-limiting examples of parameters that may indicate a new event for retraining the stimulation model include, but are not limited to, heart rate variability, blood oximetry, humidity, barometric pressure, ambient temperature, skin temperature, or accelerometer readings from an inertial measurement unit. In this way, machine learning via the cloud 801 may be used to more finely tune each person's bilateral stimulation app to more effectively help the person reduce stress and improve performance.

The present disclosure has been described in terms of improving an individual's performance by reduction in stress that can assist a person in real or imagined situations in everyday live, relieve stress or anxiety prior to surgery or a medical procedure (for themselves or a family member), relieve post-surgical and physical therapy stress during recovery.

The disclosed methods and systems provide asynchronous (or continuous) alternating bi-lateral stimulation to support the reduction of stress in persons. In various non-limiting embodiments, the bi-lateral stimulation can be selectively (manually) activated by an individual perceiving a need for reduction in stress or automatically (closed-loop) via the bi-lateral stimulation system monitoring and evaluating one or more physiological and environmental parameters. It will be appreciated that the disclosed asynchronous methods and systems provide an advantage with the overlapping time period of simultaneous stimulation which enhances the bi-lateral impact in the somatosensory areas of the person's brain. It will also be appreciated that the disclosed continuous methods and systems provide an advantage by not allowing time for the person's brain to activate the somatosensory areas of the individual's brain. The disclosed asynchronous and continuous bi-lateral stimulations regimes provides an advantage over conventional bi-lateral stimulators in ensuring that the stimulation gap commonly used in conventional bi-lateral stimulators will not allow the brain to activate the sympathetic system.

It will be appreciated that the various illustrative logical blocks/tasks/steps, modules, circuits, and method steps described in connection with the embodiments disclosed herein may be implemented as electronic hardware, computer software, or combinations of both. Some of the embodiments and implementations are described above in terms of functional and/or logical block components or modules and various processing steps. However, it should be appreciated that such block components or modules may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope as set forth in the claims.

For example, an embodiment of a system or a component may employ various integrated circuit components, for example, memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. The word exemplary is used exclusively herein to mean serving as an example, instance, or illustration. Any embodiment described herein as "exemplary" is not necessarily to be construed as preferred or advantageous over other embodiments.

The steps of a method described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC.

In this document, relational terms such as first and second, and the like may be used solely to distinguish one entity or action from another entity or action without necessarily requiring or implying any actual such relationship or order between such entities or actions. Numerical ordinals such as first, second, third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as connect or coupled to that are used in describing a relationship between different elements does not imply that a direct physical connection must be made between these elements. For example, two elements may be connected to each other physically, electronically, logically, or in any other manner, through one or more additional elements.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration in any way. Rather, the foregoing detailed description will provide those skilled in the art with a convenient road map for implementing the exemplary embodiment or exemplary embodiments.

What is claimed is:

1. A method for providing a therapeutic benefit to a conscious and active person, comprising:
   at a processor, executing a first function to determine at least one physiological parameter from a plurality of physiological sensors positioned bilaterally on the person and executing a Kalman filter function on data received from the plurality of physiological sensors to filter the data received from the plurality of physiological sensors;
   at the processor, executing a second function to determine at least one environmental parameter from a plurality of environmental sensors positioned bilaterally on the person and associated with a location of the person;
   at the processor, determining, using at least one physiological parameter and at least one environmental parameter, whether to apply bi-lateral tactile stimulation to the person;
   at the processor, activating first and second stimulators positioned bi-laterally on the person to initiate bi-lateral tactile stimulation for a therapeutically effective time period when the processor determines to apply bi-lateral tactile stimulation.

2. The method of claim 1, further comprising, at the processor, determining whether the bi-lateral tactile stimulation has mitigated stress in the person.

3. The method of claim 2, further comprising, at the processor, modifying the bi-lateral tactile stimulation and applying the modified bi-lateral tactile stimulation for a second therapeutically effective time period.

4. The method of claim 3, wherein the processor causes the modified bi-lateral tactile stimulation to be substantially uniform in speed and intensity during the second therapeutically effective time period.

5. The method of claim 3, wherein the processor causes the modified bi-lateral tactile stimulation to be substantially uniform in speed and increase in intensity during the second therapeutically effective time period.

6. The method of claim 3, wherein the processor causes the modified bi-lateral tactile stimulation to be substantially uniform in intensity and increase in speed during the second therapeutically effective time period.

7. The method of claim 3, wherein the processor causes the modified bi-lateral tactile stimulation to increase in intensity and speed during the second therapeutically effective time period.

8. The method of claim 3, wherein the processor causes the modified bi-lateral tactile stimulation to be substantially uniform in intensity and decrease in speed during the second therapeutically effective time period.

9. The method of claim 3, wherein the processor causes the modified bi-lateral tactile stimulation to be substantially uniform in speed and decrease in intensity during the second therapeutically effective time period.

10. The method of claim 1, where activating the first and second stimulators comprises the processor activating the first and second stimulators positioned bi-laterally on the person to initiate bi-lateral continuous stimulation for the therapeutically effective time period.

11. The method of claim 1, where activating the first and second stimulators comprises the processor activating the first and second stimulators positioned bi-laterally on the person to initiate bi-lateral asynchronous stimulation for the therapeutically effective time period.

12. A system for providing a therapeutic benefit to a person, comprising:
   first and second tactile stimulators configured to be bi-laterally positioned in therapeutic contact with a body of the person;
   a plurality of physiological sensors coupled to the first and second tactile stimulators;
   a plurality of environmental sensors coupled to the first and second tactile stimulators;
   a processor communicably coupled to the first and second tactile simulators, the plurality of physiological sensors and the plurality of environmental sensors, the processor configured to:
      execute a first function to determine at least one physiological parameter from the plurality of physiological sensors configured to be positioned on the person and executing a Kalman filter function on data received from the plurality of physiological sensors to filter the data received from the plurality of physiological sensors;
      execute a second function to determine at least one environmental parameter from the plurality of environmental sensors configured to be positioned bilaterally on the person and associated with the location of the person;
      determine, using at least one physiological parameter and at least one environmental parameter, whether to apply bi-lateral tactile stimulation to the person; and
      activate the first and second stimulators configured to be positioned bi-laterally on the person to initiate bi-lateral tactile stimulation for a therapeutically effective time period when the processor determines to apply bi-lateral tactile stimulation.

13. The system of claim 12, wherein the first and second tactile stimulators comprise vibrating elements.

14. The system of claim 12, wherein the first and second tactile stimulators are communicably coupled to the processor via wireless communication.

15. The system of claim 12, wherein at least one of the first and second tactile stimulators are mounted in hand-held devices.

16. The system of claim 12, wherein at least one of the first and second tactile stimulators are mounted in wearable devices.

17. The system of claim 12, wherein the processor operates to apply a second stimulation prior to cessation of a first stimulation.

18. The system of claim 12, wherein the processor operates to vary at least one of stimulation speed and stimulation intensity over the therapeutically effective time period.

* * * * *

UNITED STATES PATENT AND TRADEMARK OFFICE
CERTIFICATE OF CORRECTION

PATENT NO. : 11,033,709 B2  
APPLICATION NO. : 16/191242  
DATED : June 15, 2021  
INVENTOR(S) : Mayo et al.

Page 1 of 1

It is certified that error appears in the above-identified patent and that said Letters Patent is hereby corrected as shown below:

In the Claims

At Column 20, Claim number 1, Line number 43, should read "…physiological sensors positioned bi-laterally on the…"

At Column 20, Claim number 1, Line number 50, should read "…environmental sensors positioned bi-laterally on the…"

At Column 22, Claim number 12, Line number 15, should read "…environmental sensor configured to be positioned bi-laterally…"

Signed and Sealed this  
Twenty-fourth Day of August, 2021

Drew Hirshfeld  
*Performing the Functions and Duties of the*  
*Under Secretary of Commerce for Intellectual Property and*  
*Director of the United States Patent and Trademark Office*